US009486226B2

(12) United States Patent
Chao

(10) Patent No.: US 9,486,226 B2
(45) Date of Patent: Nov. 8, 2016

(54) TIBIAL GUIDES, TOOLS, AND TECHNIQUES FOR RESECTING THE TIBIAL PLATEAU

(71) Applicant: CONFORMIS, INC., Bedford, MA (US)

(72) Inventor: Nam T. Chao, Marlborough, MA (US)

(73) Assignee: ConforMIS, Inc., Bedford, MA (US)

( * ) Notice: Subject to any disclaimer, the term of this patent is extended or adjusted under 35 U.S.C. 154(b) by 644 days.

(21) Appl. No.: 13/865,958

(22) Filed: Apr. 18, 2013

(65) Prior Publication Data

US 2013/0296874 A1 Nov. 7, 2013

Related U.S. Application Data

(60) Provisional application No. 61/635,270, filed on Apr. 18, 2012.

(51) Int. Cl.
*A61B 17/15* (2006.01)

(52) U.S. Cl.
CPC .................... *A61B 17/157* (2013.01)

(58) Field of Classification Search
CPC .. A61B 17/157; A61B 17/15; A61B 17/151; A61B 17/152; A61B 17/154; A61B 17/155; A61B 2017/320052; A61B 2019/508
See application file for complete search history.

(56) References Cited

U.S. PATENT DOCUMENTS

| 3,314,420 A | 4/1967 | Smith et al. ............... 128/92 |
| 3,605,123 A | 9/1971 | Hahn .................................. 3/1 |
| 3,798,679 A | 3/1974 | Ewald .................................. 3/1 |
| 3,808,606 A | 5/1974 | Tronzo ................................ 3/1 |
| 3,843,975 A | 10/1974 | Tronzo ................................ 3/1 |
| 3,855,638 A | 12/1974 | Pilliar .................................. 3/1 |
| 3,938,198 A | 2/1976 | Kahn et al. ................... 3/1.912 |
| 4,052,753 A | 10/1977 | Dedo ................................... 3/1 |
| 4,055,862 A | 11/1977 | Farling ............................ 3/1.91 |
| 4,085,466 A | 4/1978 | Goodfellow et al. .......... 3/1.91 |
| 4,098,626 A | 7/1978 | Graham et al. ............. 149/19.4 |
| 4,203,444 A | 5/1980 | Bonnell et al. .............. 128/276 |
| 4,213,816 A | 7/1980 | Morris .......................... 156/245 |
| 4,340,978 A | 7/1982 | Buechel et al. ............. 3/1.911 |
| 4,368,040 A | 1/1983 | Weissman ..................... 433/36 |
| 4,436,684 A | 3/1984 | White .......................... 264/138 |
| 4,501,266 A | 2/1985 | McDaniel ..................... 128/69 |
| 4,502,161 A | 3/1985 | Wall ............................... 3/1.91 |
| 4,586,496 A | 5/1986 | Keller ......................... 128/92 E |
| 4,594,380 A | 6/1986 | Chapin et al. ............... 524/144 |
| 4,601,290 A | 7/1986 | Effron et al. ................ 128/305 |

(Continued)

FOREIGN PATENT DOCUMENTS

| DE | 2306552 | 8/1974 | ............... A61F 1/00 |
| DE | 3516743 | 11/1986 | ............... A61F 2/36 |

(Continued)

OTHER PUBLICATIONS

Andersson et al., "MacIntosh Arthroplasty in Rheumatoid Arthritis," Acta. Orthrop. Scand. 45(2):245-259 (1974).

(Continued)

*Primary Examiner* — Anu Ramana
(74) *Attorney, Agent, or Firm* — Sunstein Kann Murphy & Timbers LLP

(57) ABSTRACT

Various patient-specific tibial guide housings, patient-specific tibial guide boxes, and methods of resecting the tibial plateau are disclosed herein.

11 Claims, 18 Drawing Sheets

(56) References Cited

U.S. PATENT DOCUMENTS

| | | | |
|---|---|---|---|
| 4,609,551 A | 9/1986 | Caplan et al. | 424/95 |
| 4,627,853 A | 12/1986 | Campbell et al. | 623/16 |
| 4,715,860 A | 12/1987 | Amstutz et al. | 623/22 |
| 4,721,104 A | 1/1988 | Kaufman et al. | 623/92 |
| 4,759,350 A | 7/1988 | Dunn et al. | 128/92 VW |
| 4,769,040 A | 9/1988 | Wevers | 623/20 |
| 4,841,975 A | 6/1989 | Woolson | 128/653 |
| 4,846,835 A | 7/1989 | Grande | 623/11 |
| 4,865,607 A | 9/1989 | Witzel et al. | 623/20 |
| 4,880,429 A | 11/1989 | Stone | 623/18 |
| 4,886,258 A | 12/1989 | Scott | 269/328 |
| 4,936,862 A | 6/1990 | Walker et al. | 623/23 |
| 4,979,949 A | 12/1990 | Matsen, III et al. | 606/53 |
| 5,002,547 A | 3/1991 | Poggie et al. | 606/88 |
| 5,041,138 A | 8/1991 | Vacanti et al. | 623/16 |
| 5,053,039 A | 10/1991 | Hofmann et al. | 606/87 |
| 5,059,216 A | 10/1991 | Winters | 623/16 |
| 5,067,964 A | 11/1991 | Richmond et al. | 623/18 |
| 5,122,144 A | 6/1992 | Bert et al. | 606/88 |
| 5,129,908 A | 7/1992 | Peterson | 606/88 |
| 5,133,759 A | 7/1992 | Turner | 623/20 |
| 5,154,717 A | 10/1992 | Matsen, III et al. | 606/53 |
| 5,162,430 A | 11/1992 | Rhee et al. | 525/54.1 |
| 5,171,322 A | 12/1992 | Kenny | 623/18 |
| 5,197,985 A | 3/1993 | Caplan et al. | 623/16 |
| 5,206,023 A | 4/1993 | Hunziker | 424/423 |
| 5,226,914 A | 7/1993 | Caplan et al. | 623/16 |
| 5,234,433 A | 8/1993 | Bert et al. | 606/88 |
| 5,246,530 A | 9/1993 | Bugle et al. | 156/643 |
| 5,250,050 A | 10/1993 | Poggie et al. | 606/79 |
| 5,258,032 A | 11/1993 | Bertin | 623/20 |
| 5,270,300 A | 12/1993 | Hunziker | 514/12 |
| 5,288,797 A | 2/1994 | Khalil et al. | 524/872 |
| 5,303,148 A | 4/1994 | Mattson et al. | 364/413.01 |
| 5,306,311 A | 4/1994 | Stone et al. | 623/18 |
| 5,314,482 A | 5/1994 | Goodfellow et al. | 623/20 |
| 5,344,459 A | 9/1994 | Swartz | 623/18 |
| 5,360,446 A | 11/1994 | Kennedy | 623/16 |
| 5,368,858 A | 11/1994 | Hunziker | 424/423 |
| 5,380,332 A | 1/1995 | Ferrante | 606/79 |
| 5,387,216 A | 2/1995 | Thornhill et al. | 606/88 |
| 5,437,676 A | 8/1995 | Bouraly et al. | 606/88 |
| 5,468,787 A | 11/1995 | Braden et al. | 523/113 |
| 5,474,559 A | 12/1995 | Bertin et al. | 606/89 |
| 5,478,739 A | 12/1995 | Slivka et al. | 435/240.23 |
| 5,486,180 A | 1/1996 | Dietz et al. | 606/87 |
| 5,501,687 A | 3/1996 | Willert et al. | 606/94 |
| 5,503,162 A | 4/1996 | Athanasiou et al. | 128/774 |
| 5,523,843 A | 6/1996 | Yamane et al. | 356/363 |
| 5,540,696 A | 7/1996 | Booth, Jr. et al. | 606/88 |
| 5,542,947 A | 8/1996 | Treacy | 606/88 |
| 5,554,190 A | 9/1996 | Draenert | 623/16 |
| 5,556,432 A | 9/1996 | Kubein-Meesenburg et al. | 623/20 |
| 5,571,205 A | 11/1996 | James | 623/24 |
| 5,575,793 A | 11/1996 | Carls et al. | 606/80 |
| 5,578,037 A | 11/1996 | Sanders et al. | 606/80 |
| 5,593,450 A | 1/1997 | Scott et al. | 623/20 |
| 5,597,379 A | 1/1997 | Haines et al. | 606/80 |
| 5,601,563 A | 2/1997 | Burke et al. | 606/86 |
| 5,613,970 A | 3/1997 | Houston et al. | 606/88 |
| 5,616,146 A | 4/1997 | Murray | 606/80 |
| 5,630,820 A | 5/1997 | Todd | 606/90 |
| 5,632,745 A | 5/1997 | Schwartz | 606/75 |
| 5,649,929 A | 7/1997 | Callaway | 606/88 |
| 5,658,291 A | 8/1997 | Techiera | 606/80 |
| 5,671,741 A | 9/1997 | Lang et al. | 128/653.2 |
| 5,681,316 A | 10/1997 | DeOrio et al. | 606/88 |
| 5,682,886 A | 11/1997 | Delp et al. | 128/653.1 |
| 5,683,466 A | 11/1997 | Vitale | 623/18 |
| 5,684,562 A | 11/1997 | Fujieda | 351/212 |
| 5,688,282 A | 11/1997 | Baron et al. | 606/90 |
| 5,728,162 A | 3/1998 | Eckhoff | 623/20 |
| 5,735,277 A | 4/1998 | Schuster | 128/653.1 |
| 5,749,874 A | 5/1998 | Schwartz | 606/75 |
| 5,749,876 A | 5/1998 | Duvillier et al. | 606/88 |
| 5,768,134 A | 6/1998 | Swaelens et al. | 364/468.28 |
| 5,769,899 A | 6/1998 | Schwartz et al. | 623/18 |
| 5,776,137 A | 7/1998 | Katz | 606/88 |
| 5,786,217 A | 7/1998 | Tubo et al. | 435/402 |
| 5,795,353 A | 8/1998 | Felt | 623/18 |
| 5,800,438 A | 9/1998 | Tuke et al. | 606/90 |
| 5,827,289 A | 10/1998 | Reiley et al. | 606/86 |
| 5,830,216 A | 11/1998 | Insall et al. | 606/88 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,860,981 A | 1/1999 | Bertin et al. | 606/89 |
| 5,871,018 A | 2/1999 | Delp et al. | 128/898 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia III et al. | 364/578 |
| 5,885,296 A | 3/1999 | Masini | 606/86 |
| 5,885,297 A | 3/1999 | Matsen, III | 606/87 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,934 A | 5/1999 | Grande et al. | 435/325 |
| 5,911,723 A | 6/1999 | Ashby et al. | 606/88 |
| 5,916,220 A | 6/1999 | Masini | 606/88 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,972,385 A | 10/1999 | Liu et al. | 424/486 |
| 5,995,738 A | 11/1999 | DiGioia, III et al. | 395/500.32 |
| 6,001,895 A | 12/1999 | Harvey et al. | 523/113 |
| 6,002,859 A | 12/1999 | DiGioia, III et al. | 395/500.32 |
| 6,007,537 A | 12/1999 | Burkinshaw et al. | 606/66 |
| 6,010,509 A | 1/2000 | Delgado et al. | 606/88 |
| 6,013,103 A | 1/2000 | Kaufman et al. | 623/20 |
| 6,046,379 A | 4/2000 | Stone et al. | 623/11 |
| 6,056,754 A | 5/2000 | Haines et al. | 606/80 |
| 6,056,756 A | 5/2000 | Eng et al. | 606/87 |
| 6,057,927 A | 5/2000 | Lévesque et al. | 356/432 T |
| 6,077,270 A | 6/2000 | Katz | 606/88 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,096,043 A | 8/2000 | Techiera et al. | 606/88 |
| 6,102,916 A | 8/2000 | Masini | 606/86 |
| 6,102,955 A | 8/2000 | Mendes et al. | 623/20 |
| 6,106,529 A | 8/2000 | Techiera | 606/88 |
| 6,110,209 A | 8/2000 | Stone | 623/16.11 |
| 6,120,541 A | 9/2000 | Johnson | 623/14.12 |
| 6,126,690 A | 10/2000 | Ateshian et al. | 623/18 |
| 6,139,578 A | 10/2000 | Lee et al. | 623/16.11 |
| 6,156,069 A | 12/2000 | Amstutz | 623/22.11 |
| 6,161,080 A | 12/2000 | Aouni-Ateshian et al. | 703/11 |
| 6,187,010 B1 | 2/2001 | Masini | 606/86 |
| 6,200,606 B1 | 3/2001 | Peterson et al. | 424/574 |
| 6,203,546 B1 | 3/2001 | MacMahon | 606/87 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,251,143 B1 | 6/2001 | Schwartz et al. | 623/23.72 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,296,646 B1 | 10/2001 | Williamson | 606/90 |
| 6,299,905 B1 | 10/2001 | Peterson et al. | 424/486 |
| 6,322,588 B1 | 11/2001 | Ogle et al. | 623/1.46 |
| 6,328,765 B1 | 12/2001 | Hardwick et al. | 623/23.72 |
| 6,344,043 B1 | 2/2002 | Pappas | 606/96 |
| 6,344,059 B1 | 2/2002 | Krakovits et al. | 623/20.31 |

(56) References Cited

U.S. PATENT DOCUMENTS

| | | | |
|---|---|---|---|
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,429,013 B1 | 8/2002 | Halvorsen et al. | 435/377 |
| 6,443,988 B2 | 9/2002 | Felt et al. | 623/17.12 |
| 6,443,991 B2 | 9/2002 | Running | 623/20.27 |
| 6,444,222 B1 | 9/2002 | Asculai et al. | 424/484 |
| 6,459,948 B1 | 10/2002 | Ateshian et al. | 700/117 |
| 6,468,314 B2 | 10/2002 | Schwartz et al. | 623/23.72 |
| 6,478,799 B1 | 11/2002 | Williamson | 606/90 |
| 6,479,996 B1 | 11/2002 | Hoogeveen et al. | 324/309 |
| 6,510,334 B1 | 1/2003 | Schuster et al. | 600/407 |
| 6,520,964 B2 | 2/2003 | Tallarida et al. | 396/567 |
| 6,558,421 B1 | 5/2003 | Fell et al. | 623/14.12 |
| 6,560,476 B1 | 5/2003 | Pelletier et al. | 600/410 |
| 6,575,980 B1 | 6/2003 | Robie et al. | 606/88 |
| 6,620,168 B1 | 9/2003 | Lombardo et al. | 606/88 |
| 6,626,945 B2 | 9/2003 | Simon et al. | 623/17.19 |
| 6,626,948 B2 | 9/2003 | Storer et al. | 623/23.14 |
| 6,632,225 B2 | 10/2003 | Sanford et al. | 606/87 |
| 6,632,235 B2 | 10/2003 | Weikel et al. | 606/192 |
| 6,652,587 B2 | 11/2003 | Felt et al. | 623/20.16 |
| 6,673,077 B1 | 1/2004 | Katz | 606/88 |
| 6,679,917 B2 | 1/2004 | Ek | 623/20.14 |
| 6,702,821 B2 | 3/2004 | Bonutti | 606/88 |
| 6,712,856 B1 | 3/2004 | Carignan et al. | 623/20.35 |
| 6,905,514 B2 | 6/2005 | Carignan et al. | 623/20.35 |
| 6,916,341 B2 | 7/2005 | Rolston | 623/20.3 |
| 6,928,742 B2 | 8/2005 | Broers et al. | 33/512 |
| 6,969,393 B2 | 11/2005 | Pinczewski et al. | 606/88 |
| 7,008,430 B2 | 3/2006 | Dong et al. | 606/80 |
| 7,060,074 B2 | 6/2006 | Rosa et al. | 606/88 |
| 7,104,997 B2 | 9/2006 | Lionberger et al. | 606/88 |
| 7,115,131 B2 | 10/2006 | Engh et al. | 606/79 |
| 7,117,027 B2 | 10/2006 | Zheng et al. | 600/426 |
| 7,141,053 B2 | 11/2006 | Rosa et al. | 606/86 |
| 7,184,814 B2 | 2/2007 | Lang et al. | 600/416 |
| 7,239,908 B1 | 7/2007 | Alexander et al. | 600/427 |
| 7,245,697 B2 | 7/2007 | Lang | 378/54 |
| 7,282,054 B2 | 10/2007 | Steffensmeier et al. | 606/96 |
| 7,292,674 B2 | 11/2007 | Lang | 378/54 |
| 7,379,529 B2 | 5/2008 | Lang | 378/54 |
| 7,442,196 B2 | 10/2008 | Fisher et al. | 606/88 |
| 7,467,892 B2 | 12/2008 | Lang et al. | 378/207 |
| 7,468,075 B2 | 12/2008 | Lang et al. | 623/16.11 |
| 7,534,263 B2 | 5/2009 | Burdulis, Jr. et al. | 623/14.12 |
| 7,615,054 B1 | 11/2009 | Bonutti | 606/86 |
| 7,618,451 B2 | 11/2009 | Berez et al. | 623/14.12 |
| 7,695,477 B2 | 4/2010 | Creger et al. | 606/87 |
| 7,747,305 B2 | 6/2010 | Dean et al. | 600/407 |
| 7,806,896 B1 | 10/2010 | Bonutti | 606/86 R |
| 7,881,768 B2 | 2/2011 | Lang et al. | 600/407 |
| 7,981,158 B2 | 7/2011 | Fitz et al. | 623/17.16 |
| 7,983,777 B2 | 7/2011 | Melton et al. | 700/98 |
| 8,036,729 B2 | 10/2011 | Lang et al. | 600/407 |
| 8,062,302 B2 | 11/2011 | Lang et al. | 606/87 |
| 8,066,708 B2 | 11/2011 | Lang et al. | 606/88 |
| 8,083,745 B2 | 12/2011 | Lang et al. | 606/87 |
| 8,092,462 B2 | 1/2012 | Pinczewski et al. | 606/88 |
| 8,105,330 B2 | 1/2012 | Fitz et al. | 606/88 |
| 8,112,142 B2 | 2/2012 | Alexander et al. | 600/427 |
| 8,122,582 B2 | 2/2012 | Burdulis, Jr. et al. | 29/527.1 |
| RE43,282 E | 3/2012 | Alexander et al. | 600/427 |
| 8,167,888 B2 | 5/2012 | Steffensmeier | 606/88 |
| 8,234,097 B2 | 7/2012 | Steines et al. | 703/1 |
| 8,257,360 B2 | 9/2012 | Richard et al. | 606/88 |
| 8,265,730 B2 | 9/2012 | Alexander et al. | 600/410 |
| 8,306,601 B2 | 11/2012 | Lang et al. | 600/407 |
| 8,323,288 B2 * | 12/2012 | Zajac | A61B 17/155 606/86 R |
| 8,337,501 B2 | 12/2012 | Fitz et al. | 606/86 R |
| 8,337,507 B2 | 12/2012 | Lang et al. | 606/102 |
| 8,343,218 B2 | 1/2013 | Lang et al. | 623/16.11 |
| 8,357,166 B2 | 1/2013 | Aram et al. | 606/88 |
| 8,366,771 B2 | 2/2013 | Burdulis, Jr. et al. | 623/14.12 |
| 8,369,926 B2 | 2/2013 | Lang et al. | 600/407 |
| 8,377,066 B2 | 2/2013 | Katrana et al. | 606/86 |
| 8,377,068 B2 | 2/2013 | Aker et al. | 606/87 |
| 8,377,129 B2 | 2/2013 | Fitz et al. | 623/14.12 |
| 8,439,926 B2 | 5/2013 | Bojarski et al. | 606/88 |
| 8,460,304 B2 | 6/2013 | Fitz et al. | 606/88 |
| 2001/0001120 A1 | 5/2001 | Masini | 606/86 |
| 2001/0010023 A1 | 7/2001 | Schwartz et al. | 623/23.72 |
| 2001/0039455 A1 | 11/2001 | Simon et al. | 623/23.51 |
| 2002/0013626 A1 | 1/2002 | Geistlich et al. | 623/23.57 |
| 2002/0029038 A1 | 3/2002 | Haines | 606/54 |
| 2002/0045940 A1 | 4/2002 | Giannetti et al. | 623/11.11 |
| 2002/0059049 A1 | 5/2002 | Bradbury et al. | 703/11 |
| 2002/0068979 A1 | 6/2002 | Brown et al. | 623/20.3 |
| 2002/0072821 A1 | 6/2002 | Baker | 700/98 |
| 2002/0079601 A1 | 6/2002 | Russell et al. | 264/40.1 |
| 2002/0082703 A1 | 6/2002 | Repicci | 623/20.29 |
| 2002/0087274 A1 | 7/2002 | Alexander et al. | 702/19 |
| 2002/0106625 A1 | 8/2002 | Hung et al. | 435/1.1 |
| 2002/0115647 A1 | 8/2002 | Halvorsen et al. | 514/171 |
| 2002/0120274 A1 | 8/2002 | Overaker et al. | 606/72 |
| 2002/0120281 A1 | 8/2002 | Overaker | 606/151 |
| 2002/0127264 A1 | 9/2002 | Felt et al. | 424/423 |
| 2002/0133230 A1 | 9/2002 | Repicci | 623/14.12 |
| 2002/0143402 A1 | 10/2002 | Steinberg | 623/22.16 |
| 2002/0151986 A1 | 10/2002 | Asculai et al. | 424/484 |
| 2002/0156150 A1 | 10/2002 | Williams et al. | 523/113 |
| 2002/0173852 A1 | 11/2002 | Felt et al. | 623/20.32 |
| 2002/0183850 A1 | 12/2002 | Felt et al. | 623/20.16 |
| 2003/0028196 A1 | 2/2003 | Bonutti | 606/87 |
| 2003/0055500 A1 | 3/2003 | Fell et al. | 623/14.12 |
| 2003/0055501 A1 | 3/2003 | Fell et al. | 623/14.12 |
| 2003/0055502 A1 | 3/2003 | Lang et al. | 623/16.11 |
| 2003/0060882 A1 | 3/2003 | Fell et al. | 623/14.12 |
| 2003/0060883 A1 | 3/2003 | Fell et al. | 623/14.12 |
| 2003/0060884 A1 | 3/2003 | Fell et al. | 623/14.12 |
| 2003/0060885 A1 | 3/2003 | Fell et al. | 623/14.12 |
| 2003/0100907 A1 | 5/2003 | Rosa et al. | 606/86 |
| 2003/0100953 A1 | 5/2003 | Rosa et al. | 623/20.3 |
| 2003/0120347 A1 | 6/2003 | Steinberg | 623/22.17 |
| 2003/0158558 A1 | 8/2003 | Horn | 606/87 |
| 2003/0158606 A1 | 8/2003 | Coon et al. | 623/20.15 |
| 2003/0163137 A1 | 8/2003 | Smucker et al. | 606/87 |
| 2003/0173695 A1 | 9/2003 | Monkhouse et al. | 264/40.1 |
| 2003/0216669 A1 | 11/2003 | Lang et al. | 600/587 |
| 2003/0225457 A1 | 12/2003 | Justin et al. | 623/20.14 |
| 2003/0236521 A1 | 12/2003 | Brown et al. | 606/80 |
| 2004/0098133 A1 | 5/2004 | Carignan et al. | 623/20.35 |
| 2004/0102852 A1 | 5/2004 | Johnson et al. | 623/20.15 |
| 2004/0122521 A1 | 6/2004 | Lee et al. | 623/20.15 |
| 2004/0133276 A1 | 7/2004 | Lang et al. | 623/14.12 |
| 2004/0138754 A1 | 7/2004 | Lang et al. | 623/20.14 |
| 2004/0147927 A1 | 7/2004 | Tsougarakis et al. | 606/53 |
| 2004/0153079 A1 | 8/2004 | Tsougarakis et al. | 606/77 |
| 2004/0153162 A1 | 8/2004 | Sanford et al. | 623/20.3 |
| 2004/0153164 A1 | 8/2004 | Sanford et al. | 623/20.29 |
| 2004/0167390 A1 | 8/2004 | Alexander et al. | 600/410 |
| 2004/0167630 A1 | 8/2004 | Rolston | 623/20.14 |
| 2004/0193280 A1 | 9/2004 | Webster et al. | 623/20.33 |
| 2004/0204644 A1 | 10/2004 | Tsougarakis et al. | 600/410 |
| 2004/0204760 A1 | 10/2004 | Fitz et al. | 623/14.12 |
| 2004/0236424 A1 | 11/2004 | Berez et al. | 623/14.12 |
| 2004/0249386 A1 | 12/2004 | Faoro | 606/88 |
| 2005/0015153 A1 | 1/2005 | Goble et al. | 623/23.46 |
| 2005/0021039 A1 | 1/2005 | Cusick et al. | 606/88 |
| 2005/0043807 A1 | 2/2005 | Wood | 623/20.14 |
| 2005/0055028 A1 | 3/2005 | Haines | 606/79 |
| 2005/0085920 A1 | 4/2005 | Williamson | 623/20.14 |
| 2005/0107883 A1 | 5/2005 | Goodfried et al. | 623/20.15 |
| 2005/0107884 A1 | 5/2005 | Johnson et al. | 623/20.15 |
| 2005/0119664 A1 | 6/2005 | Carignan et al. | 606/96 |
| 2005/0143745 A1 | 6/2005 | Hodorek et al. | 606/87 |

(56) References Cited

U.S. PATENT DOCUMENTS

| | | |
|---|---|---|
| 2005/0148843 A1 | 7/2005 | Roose ............................ 600/407 |
| 2005/0171545 A1 | 8/2005 | Walsh et al. .................... 606/72 |
| 2005/0171612 A1 | 8/2005 | Rolston ...................... 623/20.19 |
| 2005/0192588 A1 | 9/2005 | Garcia ............................ 606/88 |
| 2005/0216305 A1 | 9/2005 | Funderud ........................ 705/2 |
| 2005/0234461 A1 | 10/2005 | Burdulis, Jr. et al. .......... 606/79 |
| 2005/0267584 A1 | 12/2005 | Burdulis et al. ........... 623/20.19 |
| 2006/0052795 A1 | 3/2006 | White ............................ 606/102 |
| 2006/0069318 A1 | 3/2006 | Keaveny et al. ............. 600/300 |
| 2006/0111722 A1 | 5/2006 | Bouadi ............................ 606/79 |
| 2006/0149283 A1 | 7/2006 | May et al. ...................... 606/96 |
| 2006/0200162 A1 | 9/2006 | Farling et al. .................. 606/88 |
| 2006/0235421 A1 | 10/2006 | Rosa et al. ...................... 606/88 |
| 2007/0015995 A1 | 1/2007 | Lang .............................. 600/407 |
| 2007/0073305 A1 | 3/2007 | Lionberger et al. ............. 606/87 |
| 2007/0118141 A1 | 5/2007 | Marchyn et al. ............... 606/88 |
| 2007/0198022 A1 | 8/2007 | Lang et al. ..................... 606/88 |
| 2007/0203430 A1 | 8/2007 | Lang et al. ................... 600/587 |
| 2007/0233151 A1 | 10/2007 | Chudik ............................ 606/96 |
| 2007/0233156 A1 | 10/2007 | Metzger ........................ 606/130 |
| 2007/0276224 A1 | 11/2007 | Lang et al. ................... 600/410 |
| 2007/0288030 A1 | 12/2007 | Metzger et al. ................. 606/87 |
| 2007/0293868 A1 | 12/2007 | Delfosse et al. ................ 606/88 |
| 2008/0004709 A1 | 1/2008 | O'Neill et al. ............. 623/20.35 |
| 2008/0015433 A1 | 1/2008 | Alexander et al. ........... 600/427 |
| 2008/0025463 A1 | 1/2008 | Lang ................................ 378/54 |
| 2008/0031412 A1 | 2/2008 | Lang et al. ...................... 378/54 |
| 2008/0058613 A1 | 3/2008 | Lang et al. .................... 600/300 |
| 2008/0058945 A1 | 3/2008 | Hajaj et al. ................. 623/20.14 |
| 2008/0114370 A1 | 5/2008 | Schoenefeld .................... 606/96 |
| 2008/0147072 A1 | 6/2008 | Park et al. ...................... 606/87 |
| 2008/0170659 A1 | 7/2008 | Lang et al. ...................... 378/56 |
| 2008/0195216 A1 | 8/2008 | Philipp ....................... 623/18.11 |
| 2008/0215059 A1 | 9/2008 | Carignan et al. ............... 606/96 |
| 2008/0219412 A1 | 9/2008 | Lang .............................. 378/207 |
| 2008/0243127 A1 | 10/2008 | Lang et al. ...................... 606/87 |
| 2008/0275452 A1 | 11/2008 | Lang et al. ...................... 606/88 |
| 2008/0281328 A1 | 11/2008 | Lang et al. ...................... 606/87 |
| 2008/0281329 A1 | 11/2008 | Fitz et al. ................... 623/17.16 |
| 2008/0281426 A1 | 11/2008 | Fitz et al. ................... 623/17.16 |
| 2009/0024131 A1 | 1/2009 | Metzger et al. ................. 606/88 |
| 2009/0076371 A1 | 3/2009 | Lang et al. .................... 600/407 |
| 2009/0087276 A1 | 4/2009 | Rose .............................. 409/79 |
| 2009/0088753 A1 | 4/2009 | Aram et al. .................... 606/79 |
| 2009/0088758 A1 | 4/2009 | Bennett .......................... 606/82 |
| 2009/0099567 A1 | 4/2009 | Zajac ............................... 606/79 |
| 2009/0131941 A1 | 5/2009 | Park et al. ...................... 606/87 |
| 2009/0131942 A1 | 5/2009 | Aker et al. ...................... 606/88 |
| 2009/0222014 A1 | 9/2009 | Bojarski et al. ................. 606/88 |
| 2009/0307893 A1 | 12/2009 | Burdulis, Jr. et al. ........ 29/527.1 |
| 2010/0160917 A1 | 6/2010 | Fitz et al. ........................ 606/88 |
| 2010/0168754 A1 | 7/2010 | Fitz et al. ........................ 606/88 |
| 2010/0281678 A1 | 11/2010 | Burdulis, Jr. et al. .......... 29/592 |
| 2010/0298894 A1 | 11/2010 | Bojarski et al. ............. 606/86 R |
| 2010/0305573 A1 | 12/2010 | Fitz et al. ........................ 606/87 |
| 2010/0305574 A1 | 12/2010 | Fitz et al. ........................ 606/88 |
| 2011/0066193 A1 | 3/2011 | Lang et al. .................. 606/86 R |
| 2011/0071581 A1 | 3/2011 | Lang et al. .................. 606/86 R |
| 2011/0125009 A1 | 5/2011 | Lang et al. .................... 600/425 |
| 2011/0213368 A1 | 9/2011 | Fitz et al. ........................ 606/80 |
| 2011/0213373 A1 | 9/2011 | Fitz et al. ........................ 606/87 |
| 2011/0213374 A1 | 9/2011 | Fitz et al. ........................ 606/87 |
| 2011/0213377 A1 | 9/2011 | Lang et al. ...................... 606/89 |
| 2011/0213427 A1 | 9/2011 | Fitz et al. .................... 606/86 R |
| 2011/0213428 A1 | 9/2011 | Fitz et al. .................... 606/86 R |
| 2011/0213429 A1 | 9/2011 | Lang et al. .................. 606/86 R |
| 2011/0213430 A1 | 9/2011 | Lang et al. .................. 606/86 R |
| 2011/0213431 A1 | 9/2011 | Fitz et al. .................... 606/86 R |
| 2011/0218539 A1 | 9/2011 | Fitz et al. ........................ 606/87 |
| 2011/0218584 A1 | 9/2011 | Fitz et al. .................... 606/86 R |
| 2011/0230888 A1 | 9/2011 | Lang et al. ...................... 606/87 |
| 2011/0238073 A1 | 9/2011 | Lang et al. ...................... 606/89 |
| 2011/0295329 A1 | 12/2011 | Fitz et al. .................... 606/86 R |
| 2011/0313423 A1 | 12/2011 | Lang et al. ...................... 606/87 |
| 2011/0319897 A1 | 12/2011 | Lang et al. ...................... 606/79 |
| 2011/0319900 A1 | 12/2011 | Lang et al. ...................... 606/87 |
| 2012/0029520 A1 | 2/2012 | Lang et al. ...................... 606/89 |
| 2012/0041446 A1 | 2/2012 | Wong et al. .................... 606/96 |
| 2012/0066892 A1 | 3/2012 | Lang et al. ...................... 29/592 |
| 2012/0071881 A1 | 3/2012 | Lang et al. ...................... 606/87 |
| 2012/0071882 A1 | 3/2012 | Lang et al. ...................... 606/88 |
| 2012/0071883 A1 | 3/2012 | Lang et al. ...................... 606/88 |
| 2012/0072185 A1 | 3/2012 | Lang et al. ........................ 703/1 |
| 2012/0101503 A1 | 4/2012 | Lang et al. ...................... 606/87 |
| 2012/0123422 A1 | 5/2012 | Agnihotri et al. .............. 606/89 |
| 2012/0143197 A1 | 6/2012 | Lang et al. ...................... 606/87 |
| 2012/0151730 A1 | 6/2012 | Fitz et al. .................... 29/407.01 |
| 2012/0158001 A1 | 6/2012 | Burdulis, Jr. et al. .......... 606/88 |
| 2012/0197260 A1 | 8/2012 | Fitz et al. ........................ 606/88 |
| 2012/0209394 A1 | 8/2012 | Bojarski et al. ............. 623/20.32 |
| 2012/0289966 A1 | 11/2012 | Fitz et al. ........................ 606/88 |
| 2012/0296337 A1 | 11/2012 | Fitz et al. ........................ 606/80 |
| 2013/0018379 A1 | 1/2013 | Fitz et al. ........................ 606/88 |
| 2013/0018380 A1 | 1/2013 | Fitz et al. .................... 623/14.12 |
| 2013/0018464 A1 | 1/2013 | Fitz et al. ........................ 606/88 |
| 2013/0023884 A1 | 1/2013 | Fitz et al. .................... 623/20.14 |
| 2013/0024000 A1 | 1/2013 | Bojarski et al. ............. 623/20.14 |
| 2013/0030419 A1 | 1/2013 | Fitz et al. .......................... 606/1 |
| 2013/0030441 A1 | 1/2013 | Fitz et al. ........................ 606/87 |
| 2013/0079781 A1 | 3/2013 | Fitz et al. ........................ 606/80 |
| 2013/0079876 A1 | 3/2013 | Fitz et al. .................... 623/14.12 |
| 2013/0081247 A1 | 4/2013 | Fitz et al. .................... 29/407.09 |
| 2013/0096562 A1 | 4/2013 | Fitz et al. ........................ 606/88 |
| 2013/0123792 A1 | 5/2013 | Fitz et al. ........................ 606/96 |

FOREIGN PATENT DOCUMENTS

| | | | |
|---|---|---|---|
| DE | 44 34 539 | 4/1996 | ............ A61F 2/38 |
| DE | 20303498 | 8/2003 | ............ A61B 17/15 |
| EP | 0337901 | 10/1989 | ............ A61B 17/14 |
| EP | 0528080 | 2/1993 | ............ A61F 2/30 |
| EP | 0 704 193 | 4/1996 | ............ A61F 2/30 |
| EP | 0626156 | 7/1997 | ............ A61F 2/38 |
| EP | 0613380 | 12/1999 | ............ A61L 27/00 |
| EP | 0993807 | 4/2000 | ............ A61B 17/17 |
| EP | 1074229 | 2/2001 | ............ A61F 2/38 |
| EP | 1077253 | 2/2001 | ............ C12N 5/00 |
| EP | 1120087 | 8/2001 | ............ A61B 17/06 |
| EP | 1129675 | 9/2001 | ............ A61F 2/30 |
| EP | 1132061 | 9/2001 | ............ A61F 2/28 |
| EP | 0732091 | 12/2001 | ............ A61F 2/38 |
| EP | 0896825 | 7/2002 | ............ A61L 27/00 |
| EP | 0814731 | 8/2002 | ............ A61F 2/30 |
| EP | 1234552 | 8/2002 | ............ A61F 2/00 |
| EP | 1234555 | 8/2002 | ............ A61F 2/30 |
| EP | 0809987 | 10/2002 | ............ A61F 2/38 |
| EP | 0833620 | 10/2002 | ............ A61K 9/22 |
| EP | 0530804 | 6/2004 | ............ A61L 25/00 |
| FR | 2819714 | 7/2002 | ............ A61F 2/44 |
| FR | 2918554 | 1/2009 | ............ A61B 17/17 |
| GB | 1451283 | 9/1976 | ............ A61F 1/24 |
| GB | 2291355 | 1/1996 | ............ A61F 2/38 |
| JP | 1-249049 | 10/1989 | ............ A61F 2/38 |
| JP | 8-173465 | 7/1996 | ............ A61F 2/38 |
| JP | 9-206322 | 8/1997 | ............ A61F 2/38 |
| JP | 2348373 | 10/2000 | ............ A61F 2/38 |
| JP | 2002-102236 | 4/2002 | ............ A61B 17/16 |
| WO | WO 87/02882 | 5/1987 | ............ A61F 2/38 |
| WO | WO 90/09769 | 9/1990 | ............ A61F 2/28 |
| WO | WO 93/04710 | 3/1993 | ............ A61L 25/00 |
| WO | WO 93/09819 | 5/1993 | ............ A61L 27/00 |
| WO | WO 93/25157 | 12/1993 | ............ A61B 17/57 |
| WO | WO 95/27450 | 10/1995 | ............ A61F 2/38 |
| WO | WO 95/28688 | 10/1995 | ............ G06T 15/00 |
| WO | WO 95/30390 | 11/1995 | ............ A61F 2/38 |
| WO | WO 95/32623 | 12/1995 | ............ A01N 1/02 |
| WO | WO 96/24302 | 8/1996 | ............ A61B 17/90 |
| WO | WO 97/25942 | 7/1997 | ............ A61F 2/32 |
| WO | WO 97/26847 | 7/1997 | ............ A61F 2/44 |
| WO | WO 97/27885 | 8/1997 | ............ A61L 27/00 |
| WO | WO 97/38676 | 10/1997 | ............ A61K 9/10 |
| WO | WO 98/12994 | 4/1998 | ............ A61F 2/28 |
| WO | WO 98/20816 | 5/1998 | ............ A61F 2/38 |
| WO | WO 98/30617 | 7/1998 | ............ C08G 63/12 |

(56) References Cited

FOREIGN PATENT DOCUMENTS

| WO | WO 98/32384 | 7/1998 | ............ A61B 17/58 |
|---|---|---|---|
| WO | WO 99/02654 | 1/1999 | ............ C12N 5/00 |
| WO | WO 99/08598 | 2/1999 | ............ A61B 8/00 |
| WO | WO 99/08728 | 2/1999 | ............ A61L 27/00 |
| WO | WO 99/40864 | 8/1999 | ............ A61B 17/56 |
| WO | WO 99/42061 | 8/1999 | ............ A61F 2/38 |
| WO | WO 99/47186 | 9/1999 | ............ A61L 27/00 |
| WO | WO 99/51719 | 10/1999 | ............ C12M 3/00 |
| WO | WO 99/56674 | 11/1999 | ............ A61F 2/36 |
| WO | WO 00/09179 | 2/2000 | ............ A61L 25/00 |
| WO | WO 00/15153 | 3/2000 | ............ A61F 2/38 |
| WO | WO 00/19911 | 4/2000 | ............ A61B 17/02 |
| WO | WO 00/35346 | 6/2000 | ............ A61B 5/11 |
| WO | WO 00/48550 | 8/2000 | |
| WO | WO 00/59411 | 10/2000 | ............ A61F 2/38 |
| WO | WO 00/74554 | 12/2000 | |
| WO | WO 01/10356 | 2/2001 | ............ A61F 2/46 |
| WO | WO 01/17463 | 3/2001 | ............ A61F 2/30 |
| WO | WO 01/19254 | 3/2001 | ............ A61B 17/00 |
| WO | WO 01/35968 | 5/2001 | ............ A61K 35/00 |
| WO | WO 01/45764 | 6/2001 | ............ A61L 27/36 |
| WO | WO 01/66021 | 9/2001 | ............ A61B 17/14 |
| WO | WO 01/68800 | 9/2001 | ............ C12M 3/00 |
| WO | WO 01/70142 | 9/2001 | ............ A61F 2/38 |
| WO | WO 01/91672 | 12/2001 | ............ A61F 2/36 |
| WO | WO 02/00270 | 1/2002 | ............ A61L 27/14 |
| WO | WO 02/00275 | 1/2002 | ............ A61L 31/14 |
| WO | WO 02/02158 | 1/2002 | ............ A61L 27/14 |
| WO | WO 02/22013 | 3/2002 | ............ A61B 5/055 |
| WO | WO 02/22014 | 3/2002 | ............ A61B 5/055 |
| WO | WO 02/23483 | 3/2002 | ............ G06T 11/00 |
| WO | WO 02/34310 | 5/2002 | ............ A61L 31/04 |
| WO | WO 02/36147 | 5/2002 | ............ A61K 31/04 |
| WO | WO 02/096268 | 12/2002 | |
| WO | WO 03/007788 | 1/2003 | |
| WO | WO 03/037192 | 5/2003 | ............ A61B 17/15 |
| WO | WO 03/047470 | 6/2003 | ............ A61F 2/34 |
| WO | WO 03/051210 | 6/2003 | ............ A61B 17/58 |
| WO | WO 03/055400 | 7/2003 | ............ A61B 17/74 |
| WO | WO 2004/043305 | 5/2004 | ............ A61F 2/30 |
| WO | WO 2004/049981 | 6/2004 | ............ A61F 2/46 |
| WO | WO 2005/051239 | 6/2005 | ............ A61F 2/08 |
| WO | WO 2005/051240 | 6/2005 | ............ A61F 2/08 |
| WO | WO 2006/060795 | 6/2006 | ............ A61B 17/17 |
| WO | WO 2006/127283 | 11/2006 | ............ A61B 17/17 |
| WO | WO 2007/041375 | 4/2007 | ............ A61F 2/38 |
| WO | WO 2007/092841 | 8/2007 | ............ A61B 17/15 |
| WO | WO 2008/112996 | 9/2008 | ............ A61B 17/15 |
| WO | WO 2008/117028 | 10/2008 | ............ A61B 17/15 |
| WO | WO 2008/157412 | 12/2008 | ............ A61B 17/17 |
| WO | WO 2009/009660 | 1/2009 | ............ A61F 2/30 |
| WO | WO 2009/111639 | 9/2009 | ............ A61B 17/58 |
| WO | WO 2010/121147 | 10/2010 | ............ A61B 17/90 |

OTHER PUBLICATIONS

Argenson et al., "Is There a Place for Patellofemoral Arthroplasty?," Clinical Orthopaedics and Related Research No. 321, pp. 162-167 (1995).

Birnbaum et al., "Computer-Assisted Orthopedic Surgery With Individual Templates and Comparison to Conventional Operation Method", Spine, vol. 26, No. 4, pp. 365-369, Feb. 2001.

Blum et al., "Knee Arthroplasty in Patients with Rheumatoid Arthritis," ANN. Rheum. Dis. 33 (1): 1-11 (1974).

Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).

Brandt et al., In German: "CRIGOS—Development of a Compact Robot System for Image-Guided Orthopedic Surgery," *Der Orthopäde*, Springer-Verlag, vol. 29, No. 7, pp. 645-649 (Jul. 2000).

Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).

Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).

Cameron, et al., "Review of a Failed Knee Replacement and Some Observations on the Design of a Knee Resurfacing Prosthesis," Arch. Orthop Trauma Surg. 97(2):87-89 (1980).

CAOS, "MIS meets CAOS Spring 2005 Symposium Schedule", *CAOS Spring 2005 Symposium*, pp. 1-9, May 19, 2005.

Carr et al., "Surface Interpolation with Radial Basis Functions for Medical Imaging," IEEE Transactions on Medical Imaging, IEEE, Inc. New York, vol. 16, pp. 96-107 (Feb. 1997).

Chelule et al., "Patient-Specific Template to Preserve Bone Stock in Total Knee Replacement: Preliminary Results", $15^{th}$ Annual ISTA Symposium, Sep. 2002, 1 page.

Chelule et al., "Computer Aided Design of Personalized Jigs in Total Knee Replacement", $3^{rd}$ Annual Meeting of CAOS Int'l Proc., Spain, Jun. 18, 21, 2003, pp. 58-59.

Clary et al., "Experience with the MacIntosh Knee Prosthesis," South Med. J. 65(3):265-272 (1972).

Conaty, et al., "Surgery of the Hip and Knee in Patients with Rheumatoid Arthritis," J. Bone Joint Surg. Am. 55(2):301-314 (1973).

De Winter et al., "The Richards Type II Patellofemoral Arthroplasty", Acta Orthop Scand 2001; 72 (5): 487-490.

Delp et al., "A Graphics-Based Software System to Develop and Analyze Models of Musculoskeletal Structures," Comput. Biol. Med., vol. 25, No. 1, pp. 21-34, 1995.

Farrar et al., "Computed Tomography Scan Scout Film for Measurement of Femoral Axis in Knee Arthroplasty," J. Arthroplasty, vol. 14, No. 8, pp. 1030-1031, 1999.

Froemel et al., "Computer Assisted Template Based Navigation for Total Knee Replacement", Documents presented at CAOS on Jun. 17, 2001, 4 pages.

Ghelman et al., "Kinematics of the Knee After Prosthetic Replacements", Clin. Orthop. May 1975: (108):149-157.

Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).

Hafez et al., "Computer-assisted Total Knee Arthroplasty Using Patient-specific Templating," *Clinical Orthopaedics and Related Research*, No. 444, pp. 184-192 (Mar. 2006).

Hafez et al., "Computer Assisted Total Knee Replacement: Could a Two-Piece Custom Template Replace the Complex Conventional Instrumentations?", $4^{th}$ Annual Meeting of CAOS Int'l Proc., Chicago, Jun. 16-19, 2004, pp. 63-64.

Hafez et al., "Computer-Assisted Total Hip Arthroplasty: The Present and the Future", Future Rheumatol., vol. 1, pp. 121-131, 2006.

Hastings et al., "Double Hemiarthroplasty of the Knee in Rheumatoid Arthritis, A Survey of Fifty Consecutive Cases," J. Bone Joint Surg. Br. 55(1):112-118 (1973).

Henderson et al., "Experience with the Use of the Macintosh Prosthesis in Knees of Patients with Pheumatoid Arthritis," South. Med. J. 62(11):1311-1315 (1969).

Jessop et al., "Follow-up of the MacIntosh Arthroplasty of the Knee Joint," Rheumatol Phys. Med. 11(5):217-224 (1972).

Kates, et al., "Experiences of Arthroplasty of the Rheumatoid Knee Using Macintosh Prostheses," Ann. Rheum. Dis. 28(3):328 (1969).

Kay et al., The MacIntosh Tibial Plateau Hemiprosthesis for the Rheumatoid Knee, J. Bone Joint Surg. Br. 54(2):256-262 (1972).

Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).

Kim et al., "Measurement of Femoral Neck Anteversion in 3D. Part 1: 3D Imaging Method," Med. and Viol. Eng. and Computing, vol. 38, No. 6, pp. 603-609, 2000.

(56) References Cited

OTHER PUBLICATIONS

Kshirsagar et al., "Measurement of Localized Cartilage Volume and Thickness of Human Knee Joints by Computer Analysis of Three-Dimensional Magnetic Resonance Images", Invest Radiol. May 1998, 33(5): 289-299 T. 111, V. 111.
Lam et al., "X-Ray Diagnosis: A Physician's Approach", Editor Lam, 1998, Springer-Verlag publishers, Title page and Table of Contents pgs. Only (ISBN 9813083247).
Lam et al., "Varus/Valgus Alignment of the Femoral Component in Total Knee Arthroplasty," The Knee, vol. 10, pp. 237-241, 2003.
Leenslag et al., "A Porous Composite for Reconstruction of Meniscus Lesions," Biological and Biomechanical Perform. of Biomaterials, Elsevier Science Publishers Amsterdam pp. 147-152 (1986).
Lu et al., "In vitro degradation of porous poly(L-lactic acid) foams", Biomaterials, 21(15):1595-1605, Aug. 2000.
MacIntosh, "Arthroplasty of the Knee in Rheumatoid Arthritis," Proceedings and Reports of Councils and Assotions, J. Bone & Joint Surg., vol. 48B No. (1):179 (Feb. 1966).
MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).
MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).
MacIntosh, "Hemiarthroplasty of the Knee Using a Space Occupying Prosthesis for Painful Varus and Valgus Deformities," J. Bone Joint Surg. Am. Dec. 1958:40-A:1431.
Mahaisavariya et al., "Morphological Study of the Proximal Femur: A New Method of Geometrical Assessment Using 3 Dimensional Reverse Engineering," Med. Eng. and Phys., vol. 24, pp. 617-622, 2002.
Marler et al., "Soft-Tissue Augmentation with Injectable Alginate and Syngeneic Fibroblasts", Plastic & Reconstructive Surgery, 105(6):2049-2058, May 2000.
Matsen, III et al., "Robotic Assistance in Orthopaedic Surgery: A Proof of Principle Using Distal Femoral Arthroplasty", Clinical Ortho. and Related Research, 296:178-186 (1993).
McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).
Nelson et al., "Arthroplasty and Arthrodesis of the Knee Joint," Orthop. Clin. North Am. 2 (1): 245-64 (1971).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier Mw, Inamura K (eds). Computer Assisted Radiology and Surgery. Amsterdam, Elsevier 944-949, 1997.
Portheine et al., In German: "Potentials of CT-based Planning and Template-based Procedure in Hip and Knee Surgery", Orth. Prac., vol. 36, pp. 786-791, 2000.
Portheine et al., English Translation with Certification: "Potentials of CT-based Planning and Template-based Procedure in Hip and Knee Surgery", Orth. Prac., vol. 36, pp. 786-791, 2000.
Portheine, In German: "Model-Based Operation Planning in Orthopedic Surgery", Thesis, RWTH Aachen University, Apr. 22, 2004, 90 pages.
Portheine, English Translation with Certification: "Model-Based Operation Planning in Orthopedic Surgery", Thesis, RWTH Aachen University, Apr. 22, 2004, 170 pages.

Portheine et al., In German: "Computer-Assisted Total Knee Endoprosthetics with Planning-Specific Treatement Templates", Biomed. Tech., vol. 46, Supp. vol. 1, Jan. 2001.
Portheine et al., English Translation with Certification: "Computer-Assisted Total Knee Endoprosthetics with Planning-Specific Treatement Templates", Biomed. Tech., vol. 46, Supp. vol. 1, Jan. 2001.
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher, "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.
Radermacher et al., "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher et al., "Computer Assisted Matching of Planning and Execution in Orthopedic Surgery", IEEE, EMBS, San Diego, 1993, pp. 946-947.
Radermacher, "Computer Assisted Matching of Planning and Execution in Orthopedic Surgery", Slide Presentation, San Diego, Nov. 29, 1993, 22 pages.
Radermacher et al., "Computer Integrated Advanced Orthopedics (CIAO)", $2^{nd}$ European Conference on Eng. and Med., presented Apr. 26, 1993, 12 pages.
Radermacher et al., "Surgical Therapy Technology", Helmholtz-Institut Aachen Research Report, 1993-1994, pp. 189-219.
Radermacher et al., "Computer Assisted Orthopedic Surgery by Means of Individual Templates •Aspects and Analysis of Potential Applications•" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Radermacher, "Image Guided Orthopedic Surgery with Individual Templates", Helmhotz-Institute for Biomed. Eng., 2 pages, 1997.
Radermacher et al., In German: "Computer-assisted operative interventions in orthopedics—are there prospects for endoprosthetics as well?", Prac. Ortho., vol. 27, pp. 149-164, 1997.
Radermacher et al., English Translation with Certification: "Computer-assisted operative interventions in orthopedics—are there prospects for endoprosthetics as well?", Prac. Ortho., vol. 27, pp. 1-17, 1997.

(56) References Cited

OTHER PUBLICATIONS

Radermacher et al., "Computer Based Decision Support for the Planning of Contact Faces for Manual Registration with Individual Templates", Helmholtz-Institute for Biomed. Eng., 7 pages, 1997-98.
Radermacher, In German: "Computer-Based Decision Support in the Selection and Evaluation of Contact Surfaces for Manual Referencing", Lecture presented at Helmholtz Meeting '98 and OSS '98, 7 pages.
Radermacher, English Translation with Certification: "Computer-Based Decision Support in the Selection and Evaluation of Contact Surfaces for Manual Referencing", Lecture presented at Helmholtz Meeting '98 and OSS '98, 8 pages.
Radermacher et al., In German: "Computer-Assisted Planning and Operation in Orthopedics", Orth. Prac. $36^{th}$ year, pp. 731-737, Dec. 2000.
Radermacher et al., English Translation with Certification: "Computer-Assisted Planning and Operation in Orthopedics", Orth. Prac. $36^{th}$ year, pp. 731-737, Dec. 2000.
Radermacher, "Template Based Navigation—An Efficient Technique for Hip and Knee Surgery", CAOS First Asian Meet, India, Mar. 27-28, 2004, pp. 44-50.
Ranawat et al., "MacIntosh Hemiarthroplasty in Rheumatoid Knee," Acta Orthop Belg., 39 (1): 1-11 (1973).
Rau et al., "Small and Neat", Medical Tech. Int'l, pp. 65, 67 and 69, 1993-94.
Schiffers et al., In German: "Planning and execution of orthopedic surgery using individualized templates," Der Orthopäde, Springer-Verlag, vol. 29, No. 7, pp. 636-640, (Jul. 2000).
Schiffers et al., English Translation with Certification: "Planning and execution of orthopedic surgery using individualized templates," Der Orthopäde, Springer-Verlag, vol. 29, No. 7, pp. 636-640, (Jul. 2000).
Schkommadau et al., "Clinical Application of Individual Templates for Pedicle Screw Placement in Comparison to Computer Navigation", Poster presented at CAOS, Feb. 18, 2000, 1 page.
Schkommadau et al., In German: "Clinical Experience With the Individual Template Technique", Orth. Prac., vol. 37, No. 1, pp. 19-22, 2001.
Schkommadau et al., English Translation with Certification: "Clinical Experience With the Individual Template Technique", Orth. Prac., vol. 37, No. 1, pp. 19-22, 2001.
Schorn et al., "MacIntosh Arthroplasty in Rheumatoid Arthritis," Rheumatol Rehabil. Aug. 1978:17(3):155-163.
Seel et al., "Three-Dimensional Planning and Virtual Radiographs in Revision Total Hip Arthroplasty for Instability", Clinical Orthopaedics and Related Research, No. 442, pp. 35-38, Jan. 2006.
Slone et al., "Body CT: A Practical Approach", Editor Slone, 1999 McGraw-Hill publishers, Title page and Table of Contents pgs. Only (ISBN 007058219).
Staudte et al., In German: "Computer-Assisted Operation Planning and Technique in Orthopedics", North Rhine-Westphalia Acad. for Sciences, Lecture N.444, ISSN 0944-8799, 2000, 17 pages.
Staudte et al., English Translation with Certification: "Computer-Assisted Operation Planning and Technique in Orthopedics", North Rhine-Westphalia Acad. for Sciences, Lecture N.444, ISSN 0944-8799, 2000, 34 pages.
Stauffer et al., "The MacIntosh Prosthesis. Prospective Clinical and Gait Evaluation," Arch. Surg. 110(6):717-720 (1975).
Stout et al., "X-Ray Structure Determination: A Practical Guide", 2nd Ed. Editors Stout and Jensen, 1989, John Wiley & Sons, Title page and Table of Contents pgs. Only (ISBN 0471607118).
Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Testi et al., "Border Tracing Algorithm Implementation for the Femoral Geometry Reconstruction," Comp. Meth. and Programs in Biomed., vol. 65, pp. 175-182, 2001.
Thoma et al., In German: "Use of a New Subtraction Procedure Based on Three-Dimensional CT Scans for the Individual Treatment of Bone Defects in the Hip and Knee," Journal DGPW, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," Journal DGPW, No. 17, pp. 27-28 (May 1999).
Thoma et al., In German: "Custom-made knee endoprosthetics using subtraction data of three-dimensional CT scans—A new approach," Der Orthopäde, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," Der Orthopäde, Springer-Verlag, vol. 29, No. 7, pp. 641-644, (Jul. 2000).
Vande Berg et al., "Assessment of Knee Cartilage in Cadavers With Dual-Detector Spiral CT Arthrography and MR Imaging", Radiology, Feb. 2002: 222(2): 430-435.
Wiese et al., "Biomaterial properties and biocompatibility in cell culture of a novel self-inflating hydrogel tissue expander", J. Biomedical Materials Research Part A, 54(2):179-188, Nov. 2000.
Wordsworth et al., "MacIntosh Arthroplasty for the Rheumatoid Knee: A 10-year Follow Up," Ann. Rheum. Dis. 44(11):738-741 (1985).
Yusof et al., "Preparation and characterization of chitin beads as a wound dressing precursor", J. Biomedical Materials Research Part A, 54(1):59-68, Oct. 2000.
Bromberg & Sunstein LLP, Amendment dated Sep. 22, 2008, pertaining to U.S. Appl. No. 09/882,363, 15 pages.
Bromberg & Sunstein LLP, Amendment dated Aug. 12, 2008, pertaining to U.S. Appl. No. 11/002,573, 25 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Amendment dated Jun. 28, 2010 pertaining to U.S. Appl. No. 11/410,515, 16 pages.
Bromberg & Sunstein LLP, Amendment dated Jun. 30, 2009, pertaining to U.S. Appl. No. 11/410,515, 18 pages.
European Patent Office, European Search Report—Application No. 09716738.1 dated Feb. 6, 2012, 10 pages.
European Patent Office, European Search Report—Application No. 12170854.9-1526, dated Oct. 9, 2012, 6 pages.
European Patent Office, European Search Report—Application No. EP 03790194, dated Jul. 13, 2006, 5 pages.
European Patent Office, Extended European Search Report—Application No. 10181149.5-1526 dated Apr. 19, 2012, 9 pages.
European Patent Office, Extended European Search Report—Application No. 10181198.2-1526 dated Apr. 19, 2012, 9 pages.
European Patent Office, Extended European Search Report—Application No. 10765271.1-2310, dated Dec. 19, 2012, 6 pages.
European Patent Office, Extended European Search Report—European Application No. 10181743.5-2310, dated Mar. 11, 2011, 6 pages.
European Patent Office, Supplementary European Search Report Application No. 04812187.5, dated Sep. 27, 2007, 3 pages.
International Searching Authority, International Preliminary Report on Patentability—International Application No. PCT/US2005/044008, dated Jun. 14, 2007, together with the Written Opinion of the International Searching Authority, 8 pages.
International Searching Authority, International Search Report—International Application No. PCT/US03/38158, dated Feb. 23, 2005, 7 pages.
International Searching Authority, International Search Report—International Application No. PCT/US04/39616, dated Mar. 28, 2005, together with the Written Opinion of the International Searching Authority, 6 pages.

(56) References Cited

OTHER PUBLICATIONS

International Searching Authority, International Search Report—International Application No. PCT/US10/31415, dated Jun. 29, 2010, together with the Written Opinion of the International Searching Authority, 9 pages.
International Searching Authority, International Search Report—International Application No. PCT/US2005/044008, dated Mar. 30, 2006, together with the Written Opinion of the International Searching Authority, 12 pages.
International Searching Authority, International Search Report—International Application No. PCT/US2006/045172, dated Apr. 19, 2007, 12 pages.
International Searching Authority, International Search Report—International Application No. PCT/US2007/061681, dated Sep. 7, 2007, together with the Written Opinion of the International Searching Authority, 12 pages.
International Searching Authority, International Search Report—International Application No. PCT/US2008/057045, dated Jul. 15, 2008, together with the Written Opinion of the International Searching Authority, 13 pages.
International Searching Authority, International Search Report—International Application No. PCT/US2008/066994, dated Feb. 19, 2009, together with the Written Opinion of the International Searching Authority, 16 pages.
International Searching Authority, International Search Report—International Application No. PCT/US2009/036189, dated Jul. 13, 2009, together with the Written Opinion of the International Searching Authority, 11 pages.
International Searching Authority, Invitation to Pay Additional Fees, and Where Applicable, Protest Fee—International Application No. PCT/US2008/066994, dated Oct. 21, 2008, 5 pages.
United States Patent and Trademark Office, Notice of Allowance dated Aug. 5, 2011, pertaining to U.S. Appl. No. 10/764,010, 14 pages.
United States Patent and Trademark Office, Notice of Allowance dated Dec. 16, 2010, pertaining to U.S. Appl. No. 10/764,010, 11 pages.
United States Patent and Trademark Office, Notice of Allowance dated Nov. 24, 2010, pertaining to U.S. Appl. No. 11/739,326, 8 pages.
United States Patent and Trademark Office, Office Action dated Apr. 20, 2010, pertaining to U.S. Appl. No. 11/739,326, 13 pages.
United States Patent and Trademark Office, Office Action dated Apr. 20, 2011, pertaining to U.S. Appl. No. 12/135,612, 13 pages.
United States Patent and Trademark Office, Office Action dated Aug. 2, 2010 pertaining to U.S. Appl. No. 11/769,434, 83 pages.
United States Patent and Trademark Office, Office Action dated Dec. 28, 2009, pertaining to U.S. Appl. No. 11/410,515, 43 pages.
United States Patent and Trademark Office, Office Action dated Dec. 30, 2008, pertaining to U.S. Appl. No. 11/410,515, 32 pages.
United States Patent and Trademark Office, Office Action dated Feb. 28, 2011, pertaining to U.S. Appl. No. 12/048,764, 12 pages.
United States Patent and Trademark Office, Office Action dated Jan. 13, 2012 pertaining to U.S. Appl. No. 12/776,840, 10 pages.
United States Patent and Trademark Office, Office action dated Jan. 26, 2010, pertaining to U.S. Appl. No. 11/671,745, 48 pages.
United States Patent and Trademark Office, Office Action dated Jan. 26, 2012, pertaining to U.S. Appl. No. 12/139,324, 14 pages.
United States Patent and Trademark Office, Office Action dated Jan. 29, 2009, pertaining to U.S. Appl. No. 10/724,010, 9 pages.
United States Patent and Trademark Office, Office Action dated Jan. 6, 2009, pertaining to U.S. Appl. No. 09/882,363, 9 pages.
United States Patent and Trademark Office, Office Action dated Jan. 9, 2009, pertaining to U.S. Appl. No. 10/764,010 11 pages.
United States Patent and Trademark Office, Office Action dated Jun. 23, 2011 pertaining to U.S. Appl. No. 11/410,515, 13 pages.
United States Patent and Trademark Office, Office Action dated Jun. 5, 2012, pertaining to U.S. Appl. No. 12/776,984, 7 pages.
United States Patent and Trademark Office, Office Action dated May 17, 2010, pertaining to U.S. Appl. No. 10/764,010, 12 pages.
United States Patent and Trademark Office, Office Action dated May 31, 2012, pertaining to U.S. Appl. No. 12/398,753, 7 pages.
United States Patent and Trademark Office, Office Action dated May 5, 2008, pertaining to U.S. Appl. No. 10/724,010, 13 pages.
United States Patent and Trademark Office, Office Action dated May 9, 2008, pertaining to U.S. Appl. No. 11/002,573, 17 pages.
United States Patent and Trademark Office, Office Action dated Nov. 26, 2007, pertaining to U.S. Appl. No. 11/002,573, 15 pages.
United States Patent and Trademark Office, Office Action dated Oct. 20, 2010, pertaining to U.S. Appl. No. 12/135,719, 10 pages.
United States Patent and Trademark Office, Office Action dated Oct. 23, 2009, pertaining to U.S. Appl. No. 10/764,010 (US Patent Publication No. US 2004/0167390), 13 pages.
United States Patent and Trademark Office, Office Action dated Oct. 6, 2010 pertaining to U.S. Appl. No. 11/410,515, 20 pages.
United States Patent and Trademark Office, Office Action dated Sep. 26, 2011 pertaining to U.S. Appl. No. 12/048,764, 9 pages.
Sunstein Kann Murphy & Timbers LLP, Preliminary Amendment dated Aug. 12, 2011, pertaining to U.S. Appl. No. 13/017,886, 13 pages.
Bromberg & Sunstein LLP, Preliminary Amendment dated Aug. 22, 2006, pertaining to U.S. Appl. No. 11/410,515, 10 pages.
Sunstein Kann Murphy & Timbers LLP, Preliminary Amendment dated Jul. 31, 2009 pertaining to U.S. Appl. No. 11/769,434, 44 pages.
Sunstein Kann Murphy & Timbers LLP, Preliminary Amendment dated Jul. 31, 2009, pertaining to U.S. Appl. No. 11/739,326, 19 pages.
Bromberg & Sunstein LLP, Request for Continued Examination dated Jul. 6, 2009, pertaining to U.S. Appl. No. 09/882,363, 16 pages.
Bromberg & Sunstein LLP, Request for Continued Examination and Response dated Nov. 4, 2008, pertaining to U.S. Appl. No. 10/724,010, 15 pages.
Bromberg & Sunstein LLP, Request for Continued Examination and Response dated Feb. 27, 2008, pertaining to U.S. Appl. No. 11/002,573, 19 pages.
Bromberg & Sunstein LLP, Response to Office Action dated Jan. 9, 2009, pertaining to U.S. Appl. No. 10/764,010, 25 pages.
Sunstein Kann Murphy & Timbers LLP, Response to Office Action dated Apr. 20, 2010, pertaining to U.S. Appl. No. 11/739,326, 22 pages.
Sunstein Kann Murphy & Timbers LLP, Response to Office Action dated Aug. 26, 2010, pertaining to U.S. Appl. No. 12/361,213, 22 pages.
Bromberg & Sunstein LLP, Response to Office Action dated Jan. 29, 2009, pertaining to U.S. Appl. No. 10/724,010, 16 pages.
Sunstein Kann Murphy & Timbers LLP, Response to Office Action dated May 17, 2010, pertaining to U.S. Appl. No. 10/764,010, 21 pages.
Sunstein Kann Murphy & Timbers LLP, Supplemental Amendment dated Sep. 18, 2009, pertaining to U.S. Appl. No. 09/882,363, 11 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.

\* cited by examiner

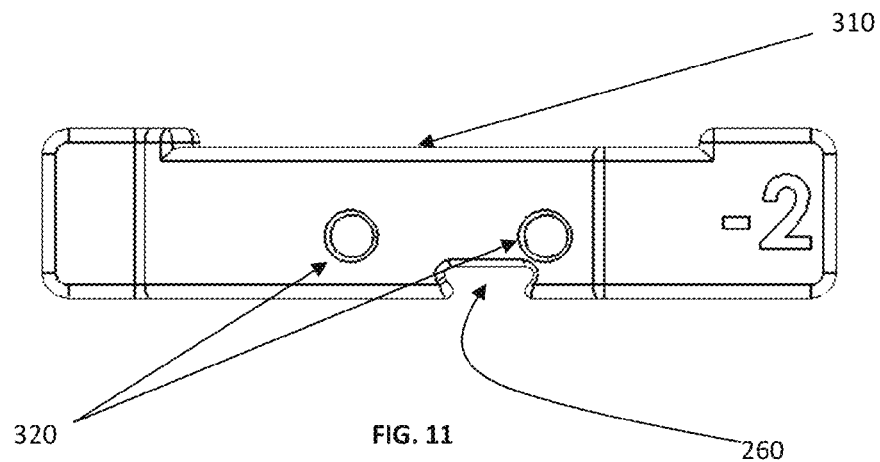
FIG. 11
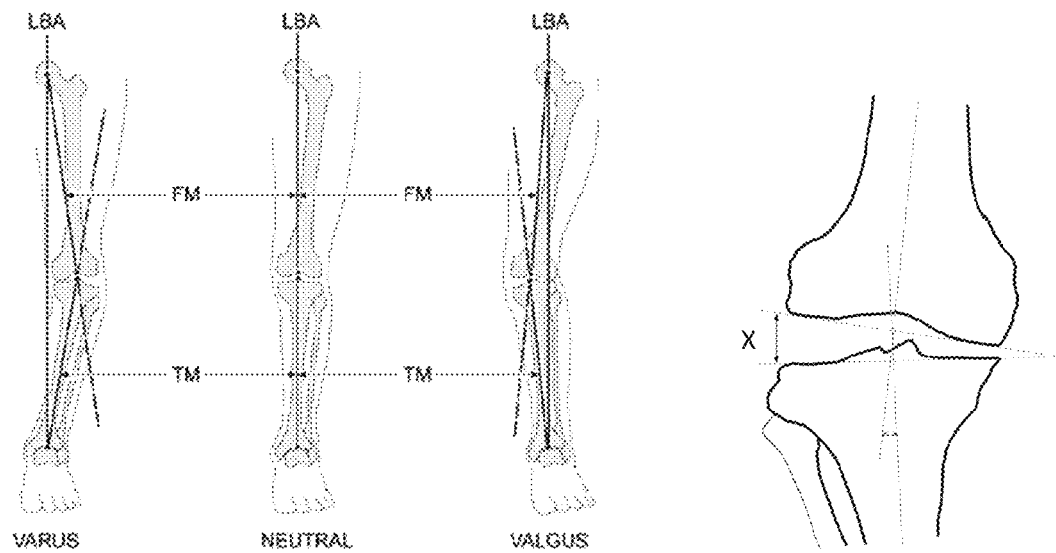
FIG. 12A
FIG. 12B
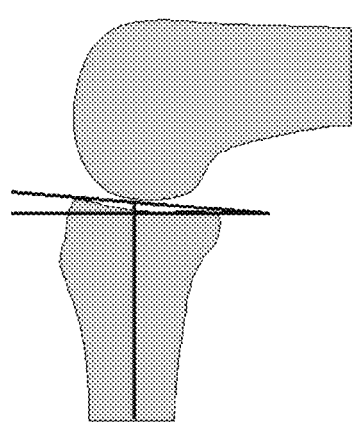
FIG. 12C

TIBIAL GUIDES, TOOLS, AND TECHNIQUES FOR RESECTING THE TIBIAL PLATEAU

RELATED APPLICATIONS

This application claims the benefit of U.S. Provisional Application Ser. No. 61/635,270, entitled "Tibial Guides, Tools, and Techniques for Resecting the Tibial Plateau" and filed Apr. 18, 2012, the disclosure of which is incorporated herein by reference in its entirety.

TECHNICAL FIELD

This disclosure relates to improved and/or patient-adapted (e.g., patient-specific and/or patient-engineered) surgical guides, tools and techniques to assist with the resection of the tibial plateau or similar bones. More specifically, the present disclosure provides a set of alignment and cutting guides and methods for use that are easier and more reliable for use by experienced and inexperienced knee surgeons.

BACKGROUND

When a patient's knee is severely damaged, such as by osteoarthritis, rheumatoid arthritis, or post-traumatic arthritis, it may be desirous to repair and/or replace portions or the entirety of the knee with a total or partial knee replacement implant. Knee replacement surgery is a well-tolerated and highly successful procedure that can help relieve pain and restore function in injured and/or severely diseased knee joints.

In a typical knee surgery, the surgeon will begin by making an incision through the various skin, fascia, and muscle layers to expose the knee joint and laterally dislocate the patella. The anterior cruciate ligament may be excised and/or the surgeon may choose to leave the posterior cruciate ligament intact—such soft tissue removal often depends on the surgeon's preference and condition(s) of the ACL/PCL. Various surgical techniques are used to remove the arthritic joint surfaces, and the tibia and femur are prepared and/or resected to accept the component artificial implants.

Preparing the surface of the tibia often requires that the surgeon resect the articular surface of the bone to receive an implant over the resected surface. The resection can include specific depths of cut(s), posterior slope(s), varus/valgus angle(s), and/or axial alignment(s) that can be unique to every patient. The specific dimensions and/or measurements desirably ensure proper positioning of the artificial joint component assembly, and accurate guiding and cutting of the tibial plateau is important to achieve the most accurate and best fit of the artificial implant components.

Traditionally, a surgeon has two options to help them prepare the tibia. The surgeon may select the traditional "freehand" method, or he/she may choose a set of surgical instruments that will assist with positioning, resection and alignment. The "freehand" method usually involves standard surgical tools available in the operating room (OR) during surgery, such as osteotomy drills and calipers for measuring. The procedure, preparation, alignment and/or resection may be more or less accurate, depending on the level of the skill and/or ability of the surgeon. Where surgical guide tools are chosen, the surgeon may employ a standard sized saw guide block or other resection guides, which desirably assist with the critical cuts required in the tibial plateau. A saw guide block or resection guide can first be attached to the patient in various ways, and then an alignment device can be used to provide a desired alignment. Once the resection guide is aligned, it can be temporarily fixed in place on the anterior side of the tibia, and the alignment device removed to allow the cutting or resection operation. While the use of such standard sized guide blocks or resection guides can improve the surgical procedure, they may not provide sufficient fine adjustments for cutting depth and/or slope, may be bulky, and may not be easy to use. The misuse or non-use of such devices can result in improper depth of cut, improper posterior slope, malalignment of varus/valgus angle(s), and poor axial alignment that may contribute to poor artificial implant positioning, instability of the joint, and poor surgical outcomes.

As a result, it has been recognized that it would be desirable to provide a more effective system of guides, tools, instruments and methods to facilitate a high degree of success in the preparation of the tibial plateau to receive an artificial joint.

SUMMARY

Some disclosed embodiments include a tibial guide housing for use in treatment of a tibia. The tibial guide housing can include a first reference arm with a patient-specific contact surface configured to conform to a first portion of the superior surface of the tibia. The tibial guide housing can also include a second reference arm having a patient-specific contact surface configured to conform to a second portion of the superior surface of the tibia. Additionally, the tibial guide housing can include at least one pin hole configured to accommodate insertion of a pin through the tibial guide housing and into the tibia. The tibial guide housing can also include a patient-specific contact surface configured to conform to a portion of an anterior surface of the tibia.

Some embodiments can include a system for preparing a tibial plateau. The system can include a tibial guide housing and one or more tibial cutting guide boxes, each of the one or more tibial cutting guide boxes. The tibial cutting guide boxes can include a patient-specific contact surface configured to conform to a portion of the anterior surface of the tibia. The tibial cutting guide boxes can also include a guide aperture configured to accommodate a surgical cutting tool and guide the cutting tool along a cutting plane having a predetermined cut depth and angle. Additionally, the tibial cutting guide boxes can include at least one pin hole configured to accommodate a pin passing into the tibia.

These and other objects, advantages, and features of the disclosure will be apparent from the following description, considered along with the accompanying drawings.

BRIEF DESCRIPTION OF THE SEVERAL VIEWS OF THE DRAWING

FIG. 11 depicts a front view of a "minus two cut depth" tibial guide box;

FIGS. 12A-12C depicts various views of a knee joint at neutral, varus and valgus angles, depicting possible posterior slopes of the knee;

DETAILED DESCRIPTION

Figure 1:
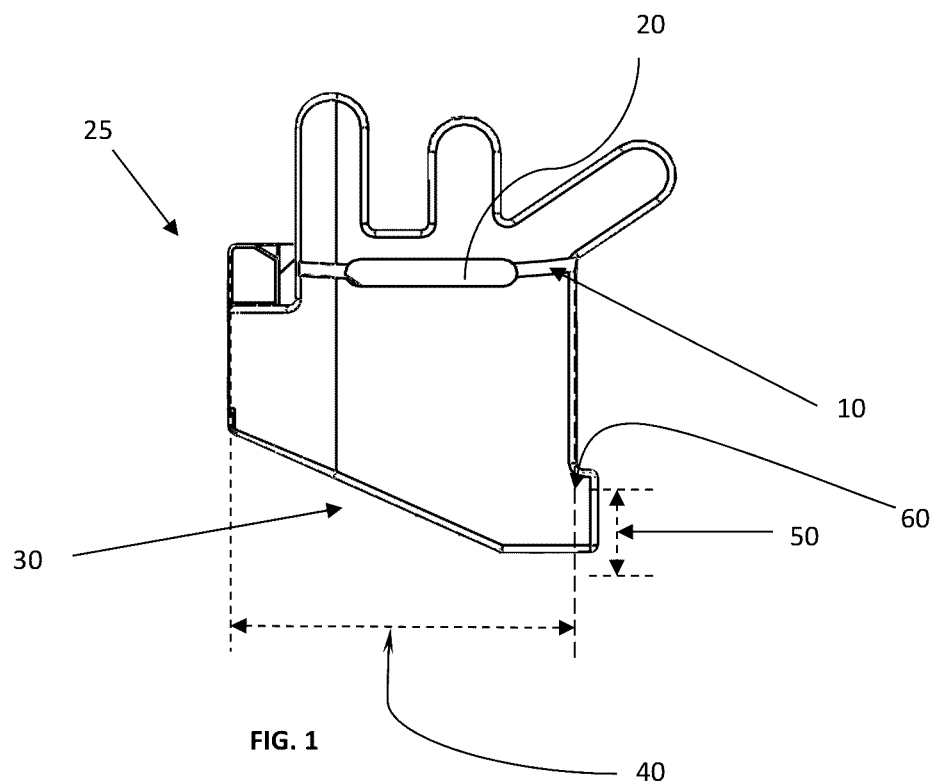
FIG. 1 depicts a top plan view of one embodiment of a tibial guide housing and/or body.

The present disclosure provides an improved patient-specific or patient-engineered tibial resection guide alignment apparatus (hereinafter "resection guide") and associated methods that desirably overcome and/or address various disadvantages of existing systems, as well as provide for controlled depth and/or slope cuts on the tibia. Various embodiments of the present disclosure may be used to facilitate total knee surgery, bicompartmental knee surgery or unicompartmental knee surgery. In addition, the various embodiments can be used for cruciate retaining surgeries or non-cruciate retaining surgeries.

Various embodiments of the present disclosure may be patient-specific or patient engineered for each surgical patient, with each tibial resection guide alignment apparatus tailored to an individual patient's joint morphology. In at least one preferred embodiment, the system may be designed as an assembly that comprises a patient specific tibial resection housing and/or body and several patient specific sized cutting blocks that can be inserted into the housing/body and used for resecting the tibial plateau.

In various embodiments, each piece of the tibial resection guide assembly can be uniquely tailored to an individual patient's anatomy, which may require images taken from the subject. The manufacturer can then design the patient-specific resection guide using the joint image from a patient or subject, wherein the image may include both normal cartilage and diseased cartilage; reconstructing dimensions of the diseased cartilage surface to correspond to normal cartilage (using, for example, a computer system) and/or bones; and designing the tibial resection guide to exactly or substantially match the dimensions of the diseased cartilage surface, the normal cartilage surface, a healthy cartilage surface, a subchondral bone surface, and/or various combinations thereof (including height, width, length, and/or reference points of the resection guide). In various alternative embodiments, the guide may substantially match an area slightly greater than the diseased cartilage surface or bone surface (or any other known size that may be applied to any patient).

The image can be, for example, an intraoperative image including a surface and/or feature detection method using any techniques known in the art, e.g., mechanical, optical, ultrasound, and known devices such as MRI, CT, ultrasound, and other image techniques known in the art. In certain embodiments, reconstruction is performed by obtaining a surface that follows the contour of the normal cartilage or the natural anatomy of the bone. The surface can be parametric and include control points that extend the contour of the normal cartilage to the diseased cartilage and/or a B-spline surface to determine the shape of at least one contact surface of the tibial resection guide to fill the areas of diseased cartilage. The images can be 2D or 3D or combination thereof to specifically design the tibial resection guide assembly.

In various embodiments, tibial resection guide assemblies constructed in accordance with various teachings described herein may be designed as extramedullary or intramedullary. Exemplary extramedullary guides or tools can be connected outside the patient's tibia, and may be designed to include an attachment for alignment rods or any other alignment mechanisms. Exemplary intramedullary alignment guides or tools can include an intramedullary rod that positioned into the central canal of the tibia with the alignment mechanism suspended from the rod.

Various embodiments can include a patient specific housing and/or body designed to include various reference points that correspond to a patient specific articular contact surface and/or subchondral bone surface (or other surface, as desired). These reference points may be perpendicular extensions or "fingers" that extend from the body to provide tibial surface anchoring. These reference points may include at least one extension, finger or arm that incorporates at least one patient specific contact surface on the articular or other surface of the tibia. The reference points may be designed to have varied lengths onto the surface of the tibia, or may be shortened to the minimum anchoring required. The reference points may be designed centrally located or can be offset to varying degrees to provide an optimal natural conforming location on the articular or other surface of the tibia to allow for stable resection.

The tibial resection guide assembly can further include one or more guide boxes that may be removably attached to the surface. The boxes may be designed to include various patient specific contact surfaces to easily mate with the anterior surface of the bone. The boxes may have at least one guide aperture for guiding a surgical cutting instrument for controlled resection of the tibia plateau. The guide boxes may also be designed to make cuts that are parallel, non-parallel, perpendicular, or non-perpendicular to other cuts.

The tibial guide boxes can be designed as removable or permanent. If the tibial guide boxes are removable, they may have a sliding mechanism that allows for easy insertion into the tibial guide resection housing and/or body. They may include other connection arrangements, including rail systems, quick connects, or other similar mechanisms for insertion into and/or connection to the guide resection housing and/or body.

Various aspects of the disclosed embodiments may be used and/or applied to a variety of other joints, such as the shoulder, hip, and wrist.

Tibial Guide Assembly Apparatus

Described herein are various embodiments of surgical tools and methods for accurately preparing the medial and lateral tibial plateau such that the plane of each cut across the bone ends will be appropriate to receive the portions of a knee prosthesis selected to reflect the spacing distance and size of the respective bone ends, so that one or more artificial knee joint components will properly and optimally replace the mechanical functioning of a normal knee.

In various embodiments, the tibial plateau preparation assembly can include: a tibial guide housing, one or more tibial cutting guide boxes with a cutting platform with a tibial depth resection guide, and optional attachment of an alignment rod. In practice, a surgeon, after opening and/or accessing the damaged knee area, may use the tibial guide assembly to prepare medial and lateral ends of a patient's tibia to receive appropriate knee components, such as a tibial tray and insert.

FIG. 1 depicts a top view of a tibial guide housing and/or body 25. The tibial housing is equipped with a variety of features that will assist the surgeon in his preparation of the tibial plateau; it is designed with a viewing window 20, an alignment indicator 10, an angled low profile body 30 and 40 and ergonomic features 50 and 60. First, the tibial guide housing contains a viewing window 20 to assist the surgeon in placement on the anterior surface of the tibia. This window will allow the surgeon to view the peripheral edge of the anterior surface of the tibia. The window, as depicted in FIG. 1, is designed substantially similar to the width of the tibial guide housing because it maximizes viewing capacity, but may be designed to have a smaller width or a larger height to accommodate the surgeon's need. The dimensions of this window may be designed as standard sizes or shapes or may be patient-specific to accommodate the tibial anatomy. The window may be a variety of shapes such as "Z," or curved shaped, or "L" shaped.

A second feature is the alignment indicator 10. This indicator provides the surgeon with visual assistance that the housing is firmly planted on the anterior surface of the tibia. The present tibial guide housing has the alignment indicator 10 designed as a small channel. However, the manufacturer may choose to design this indicator on the surface of the housing with additional visual indicators such as an arrow. The alignment indicator may be any size, shape or dimension. The alignment indicator may also be designed as patient specific to match or substantially match the perimeter of the tibia.

The tibial guide housing may be designed to have a low profile for surgery. A design that is low profile has many advantages because there is often minimal space available above and/or adjacent to the tibia during cruciate ligament retaining procedures. The angled front 30 of the tibial guide housing achieves this purpose. Also, the width 40 of the housing is also smaller than other available cutting guides. The width of the housing 40 minimizes the profile of the cutting guide and may be designed as patient specific.

The tibial guide housing may be designed to have ergonomic features, such as the extension tab 50 and radiused edges 60. The extension tab 50 allows the surgeon to grasp and handle the tibial guide housing by its edge. The edges within the extension tab are radiused 60 to provide for easy finger transition and no sharp edges. The width of this extension may be designed with varying heights or shapes. The manufacturer may design this with a "U" shape or other variety of shapes to accommodate holding of the housing.

Figure 2:
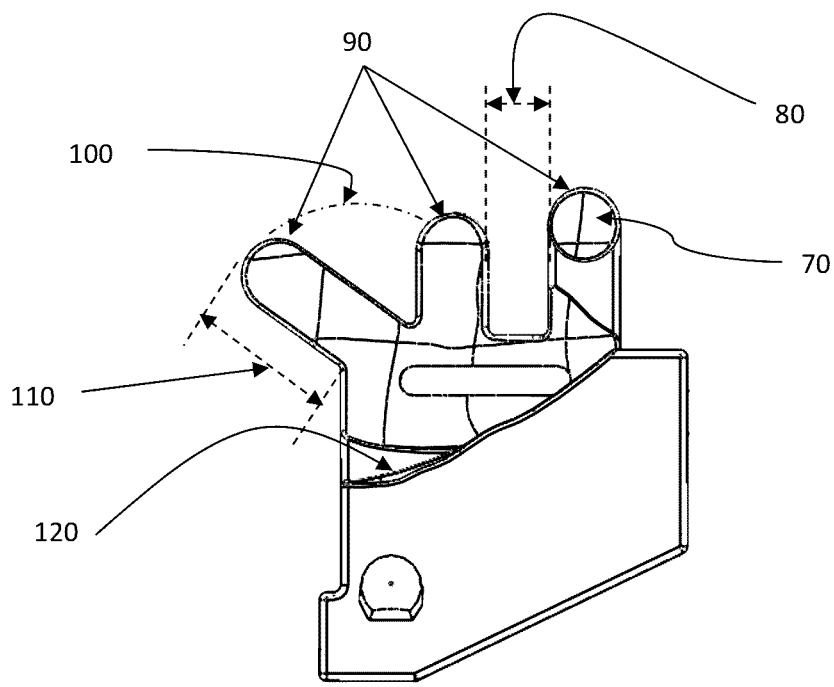
FIG. 2 depicts a bottom plan view of the tibial guide housing of FIG. 1.

FIG. 2 depicts a bottom view of the tibial guide housing, showing the reference arms 90, and the patient-specific contact surfaces 70 and 120. The tibial guide housing may be designed with specific reference extensions/arms 90 to help the surgeon find the natural, conforming position for more accurate resection. If the surgeon is resecting the medial side of the tibial plateau, the surgeon will place the reference arms 90 on the articular surface of the tibia and move it around until the reference arms finds their own natural, conforming position(s). The reference arms may be designed with at least one reference arm, but in various preferred embodiments can include three reference arms. The reference arms may respectively be titled as the "medial reference arm," which may align with the center of the medial tibial plateau, the "center reference arm," which can align between the tibial spines, and the "left reference arm," which can align with the center of the tibia. Each reference arm can be made patient specific or be made with standard available sizes retrieved from a database. The reference arms spacing 80 may vary with every patient, or a set spacing may be designed or incorporated between each reference arm. In addition, the medial reference arm and the center reference arm may also have patient-specific angles 100 designed into the housing, or angles 100 may be set standard angles derived from a database. The length 110 of each reference arm may also vary between each patient (i.e., be a patient-specific length). In various embodiments, the tibial guide housing surfaces 120 and 70 that contact the anterior portions of the tibia will be patient specific to provide a secure and conforming fit.

Figure 3:
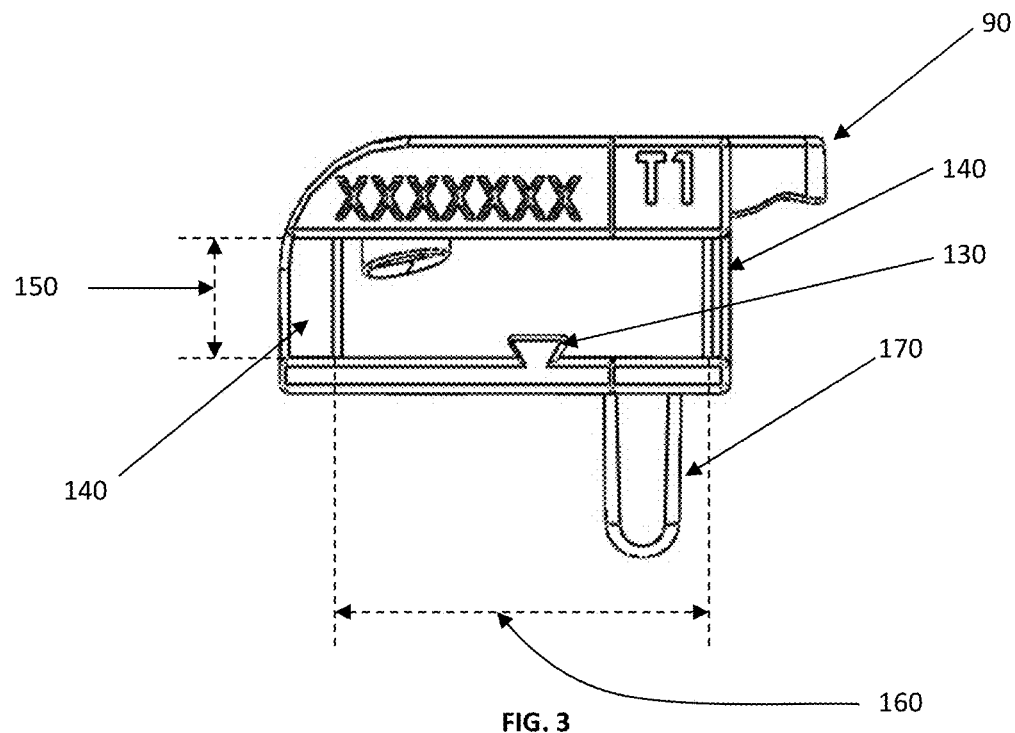
FIG. 3 depicts a front view of the tibial guide housing of FIG. 1.

FIG. 3 depicts a front view of the tibial guide housing. The front view highlights specific features such as the dovetail rail 130, the alignment rod attachment 170, the low profile width 160 and height 150 for tibial guide box insertion, and the tibial guide box positive stops 140. The dovetail rail 130 is designed within the tibial guide housing to allow and/or facilitate easy insertion and securement of the tibial guide boxes (see FIG. 8A-8C). This also allows locking of the tray into the housing and prevents any unnecessary motion or movement during cutting. The tibial guide boxes may be secured into the tibial guide housing using any mechanism that is known in the art. If desired, the tibial guide boxes may be secured by inserting the boxes into the housing and securing by set screws, by press fit, by snap tabs, or other equivalent mechanisms. Alternatively, the bottom may be designed with a recessed tray that seats the tibial guide box.

The tibial guide housing height 150 and width 160 may be designed specifically to fit one or more of the tibial guide cutting boxes. The dimensions may be minimized to provide a low profile for the assembly, or they may have different shapes to facilitate insertion of the guide boxes. The dimensions may also be patient-specific. The height 150 and/or width 160 may vary depending on the morphology or other features of the damaged or diseased tibia and articular surfaces. The tibial guide housing may also provide positive stop walls 140 to prevent the tibial guide boxes from sliding forward or other directions as well as to potentially prevent the surgeon from over-exerting pressure during insertion. The surgeon can insert the guide box into the guide housing until it reaches a detent or stop to provide accurate alignment. The tibial guide housing may also include an alignment leg 170 to allow attachment of the tibial alignment rod to the body.

Figure 4:
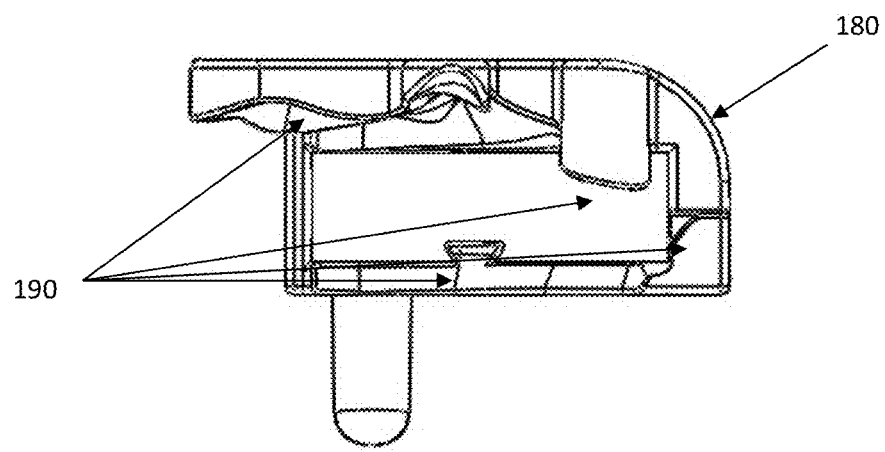
FIG. 4 depicts a back view of the tibial guide housing of FIG. 1.

FIG. 4 depicts a back view of the tibial guide housing and highlights the patient contact surfaces 190 and the curved exterior wall 180. The contact surfaces 190 may be patient specific. The image data evaluated to manufacture the housing can be used to design the surface that contacts or mates with the articular surface of the tibial plateau, thus having or approximating a patient specific shape(s). Such features can allow stability and more secure attachment when resecting or cutting is taking place. The exterior wall can be radiused 180, as desired, to eliminate, reduce or minimize soft tissue irritation.

Figure 5:
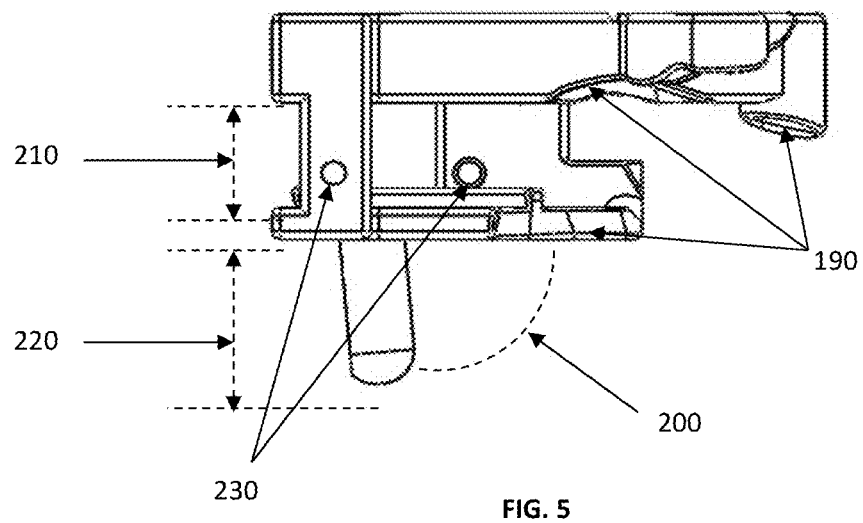
FIG. 5 depicts a right-side view of the tibial guide housing of FIG. 1.

FIG. 5 depicts a right-side view of the tibial guide housing and/or body. In this view, various detent receiver holes 230 are shown. These detent receiver holes 230 can receive a tibial guide insert box, and in various embodiments the successful insertion can be accompanied by an audible sound or other indication to the surgeon when the box is secured in place. The detent receiver holes 230 can be designed as a receiver for tabs, levers, etc., or they may have different shapes. The alignment leg angle 200 and the alignment leg 220 are also shown in this view. The angle and the length of the alignment leg may be designed as patient specific for increased accuracy in the alignment of the housing to the center axis of the tibia. The alignment leg angle 200 and the height 220 may also be designed as standard dimensions that can be determined from evaluations from a database of various patients. The alignment leg may also be designed to include various connection types, including press fit insertion. For easy removal, the alignment leg may include a quick release/connection mechanism for the surgeon's use that can prevent excessive upward force on the tibial guide housing. This side view also highlights an example of the patient specific nature of the contact surfaces 190 of the tibial guide housing.

Figure 6:
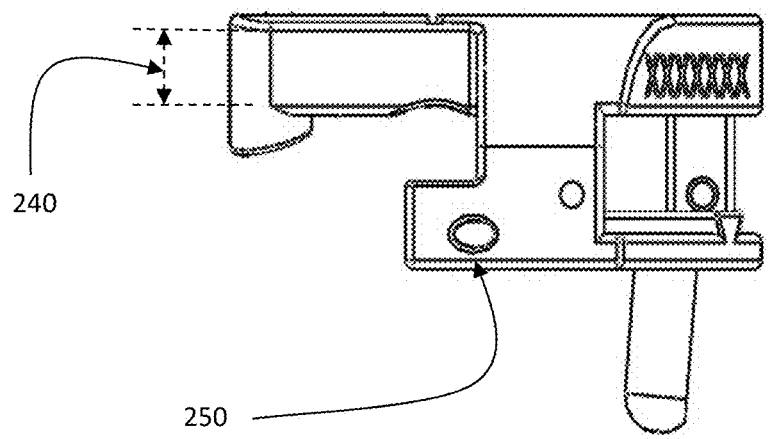
FIG. 6 depicts a left-side view of the tibial guide housing of FIG. 1.
Figure 7:
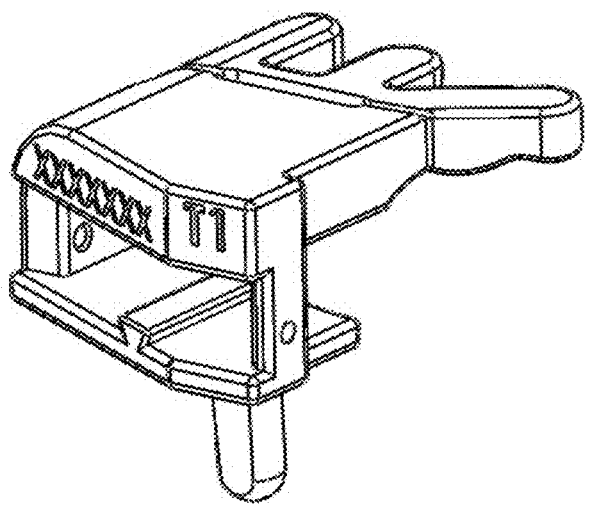
FIG. 7 depicts an isometric perspective view of the tibial guide housing of FIG. 1.

FIG. 6 depicts a left-side view of the tibial guide housing and/or body. This view highlights the relative thickness/height 240 of a reference arm, as well as an exemplary pin hole 250. The reference arm thickness/height 240 may be designed as patient specific. Each reference arm may have different thicknesses/heights to accommodate the diseased patient's surface. The thickness/height of each arm may also be designed to have standard dimensions as derived from a database of similar patients. The tibial guide housing may have one or more pin holes 250 to help secure the housing to the tibia. The pin holes may be designed large enough to accommodate a drill and to insert pins for visual guidance or location on the tibia.

Figure 8A:
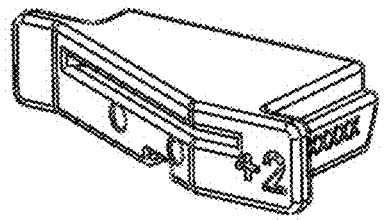
FIGS. 8A-8C depict isometric perspective views of different embodiments of tibial guide boxes having various cut depths constructed in accordance with the teaching of the present invention.
Figure 8B:
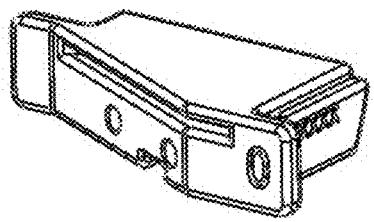
Figure 8C:
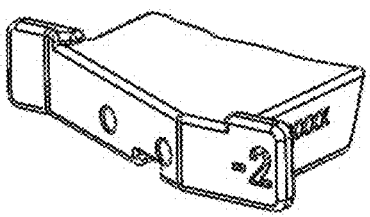

FIGS. 8A-8C depict isometric perspective views of various embodiments of different tibial guide boxes that can be used with various features disclosed herein, with various available cut depths included in one preferred embodiment. FIG. 8A shows the "+2" tibial guide box that can be employed by the surgeon to make a primary cut to the tibia. This box, along with other system features, desirably facilitates the surgeon's ability to adjust the resection or cut of the tibial plateau after a primary cut has been completed. In the embodiment shown in FIG. 8B, the primary cut can be defined as the "0" tibial guide box. In various procedures, the "0" guide box will be inserted and utilized by the surgeon to make the primary cut and may be, in various embodiments, a patient-specific selected or derived depth. FIG. 8C shows a "−2" guide box which can also allow the surgeon to adjust the cut after the primary cut has been made. Many other cut depths can be created to allow the surgeon to make additional controlled depth cuts on the tibial plateau.

Figure 9:
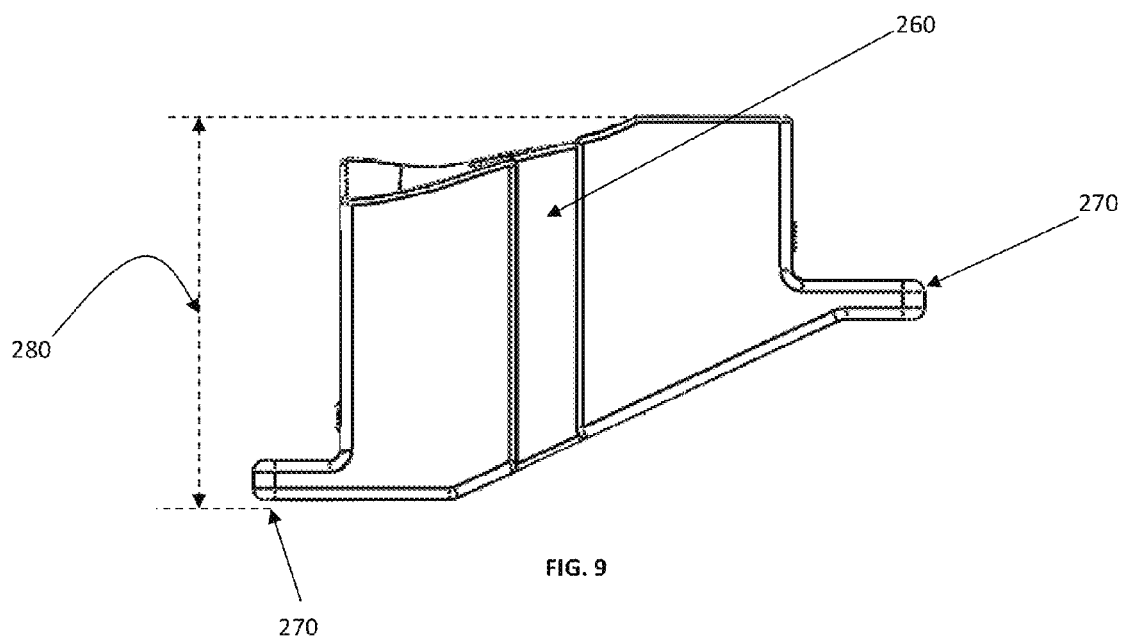
FIG. 9 depicts a bottom plan view of a tibial guide box.
Figure 10:
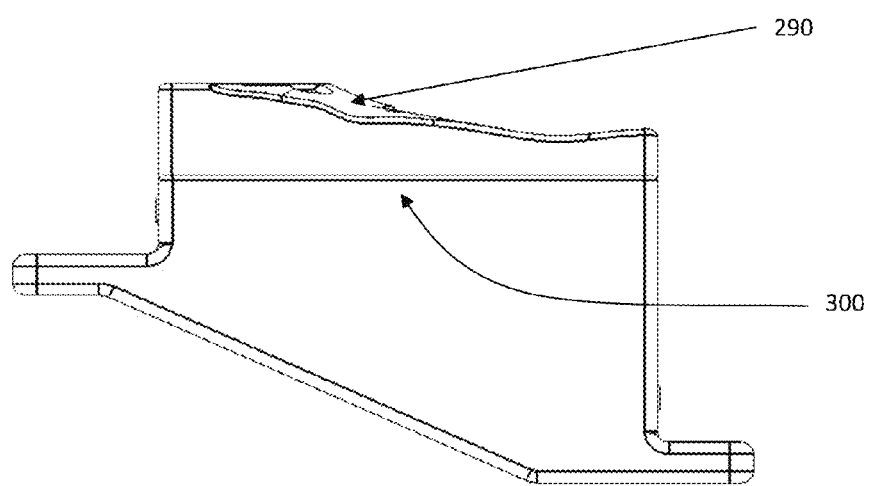
FIG. 10 depicts a top plan view of a tibial guide box.

FIGS. 9 and 10 depict the bottom and top plan views, respectively, of a tibial guide box. In these embodiments, the bottom view of the guide box shows a dovetail rail 260, and the positive stop tabs 270. The dovetail rail 260 may have varying widths or lengths for quick and guided insertion of the tibial guide boxes. The positive stop tabs 270 are designed to extend to contact the positive stop walls 140. FIG. 10 shows that the cut guide cover 300 need not necessarily extend the full depth of the tibial guide box. However, the cut guide cover may be designed to reach the entire length/depth of the tibial guide box. In addition, the cut guide cover may be manufactured out of variety of materials that would withstand an oscillating or reciprocating saw. It can be manufactured out of biocompatible metals and/or plastics.

FIG. 11 depicts a front view of a minus two cut depth guide box. This specific guide cut box need not necessarily have a cut guide cover 300 because it can use the roof of the tibial guide housing as a portion of the cut guide cover. In contrast, FIGS. 8A and 8B depict guide cut covers 300 that are designed in portions of the boxes. FIG. 11 further depicts two pin holes 320 that may be incorporated into the design of each tibial guide cut box. The tibial guide box may have pin holes 320 to help secure the box to the tibia. The pin holes may be designed large enough to accommodate a drill and to insert pins for visual guidance or location on the tibia. Also, additional pin holes may be designed into the guide box or guide housing. As previously noted, the "−2" guide box still can guide 310 the reciprocating saw or the oscillating saw by using the roof the tibial guide housing as a guide boundary. This guided slot 310 may be manufactured to specific dimensions to accommodate standard oscillating or reciprocating bone saws. In another embodiment, the guided slot 310 may also incorporate various angles, shaped and/or configurations, including different features to accommodate different varus/valgus (see FIG. 13) and/or anterior/posterior angles (see FIG. 12C) designed within the box.

Figure 13A:
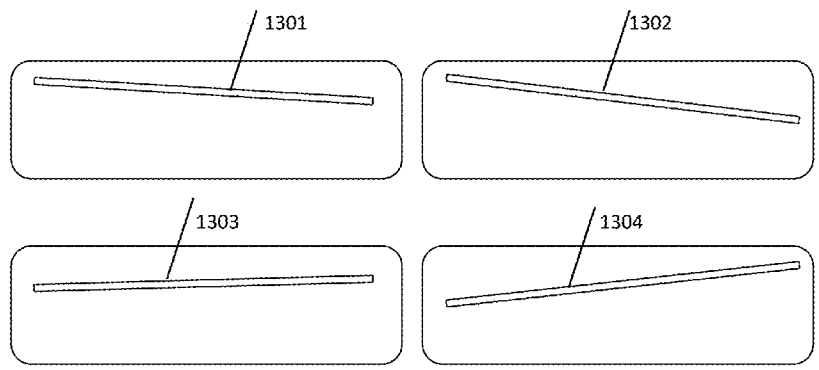
FIGS. 13A and 13B generally depict various examples varus and valgus guide cut slots that can be designed as standard and/or adjustable features, for adjusting varus/valgus angles.
Figure 13B:
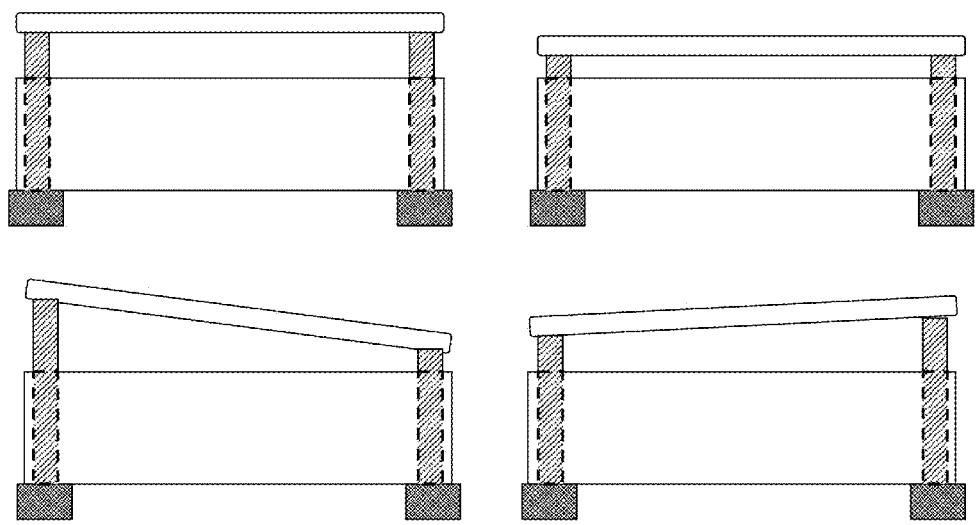

FIGS. 12A and 12B depict a human knee with exemplary varus, neutral and valgus orientations, and various exemplary angles that a cut guided slot 30 or other tool may incorporate to accommodate and/or correct such orientations. In a varus knee, this line passes medial to the knee and a moment arm is created, which increases force across the medial compartment of the knee. In a valgus knee, the load-bearing axis (LBA) passes lateral to the knee, and the resulting moment arm increases force across the lateral compartment of the knee. In various embodiments, specifically designed tibial guide boxes that incorporate patient specific varus/valgus angles could be employed to reduce and/or correct such deformities, desirably reducing abnormal forces in the artificial knee joint, and returning the LBA to a normal functioning knee at its neutral position. FIG. 13A depicts various cut guide slot angulations that, when used in conjunction with a tibial guide box as described herein, can generally be employed to alter the resulting varus or valgus angles of one or more tibial cut planes. FIG. 13B depicts one alternative embodiment of a guide tool that incorporates an adjustment mechanism 322 that can be employed and adjusted to alter the cut angle. The adjustment mechanism could include a screw thread or other mechanism that allows a wide variation in the cut plane angle, which could include larger wedges to accommodate more severe varus/valgus angles. In various embodiment, the guide tool with the adjustable mechanism could be sized and configured to fit into the standard guided slots 1301-1304 as shown in FIG. 13A.

Figure 24:
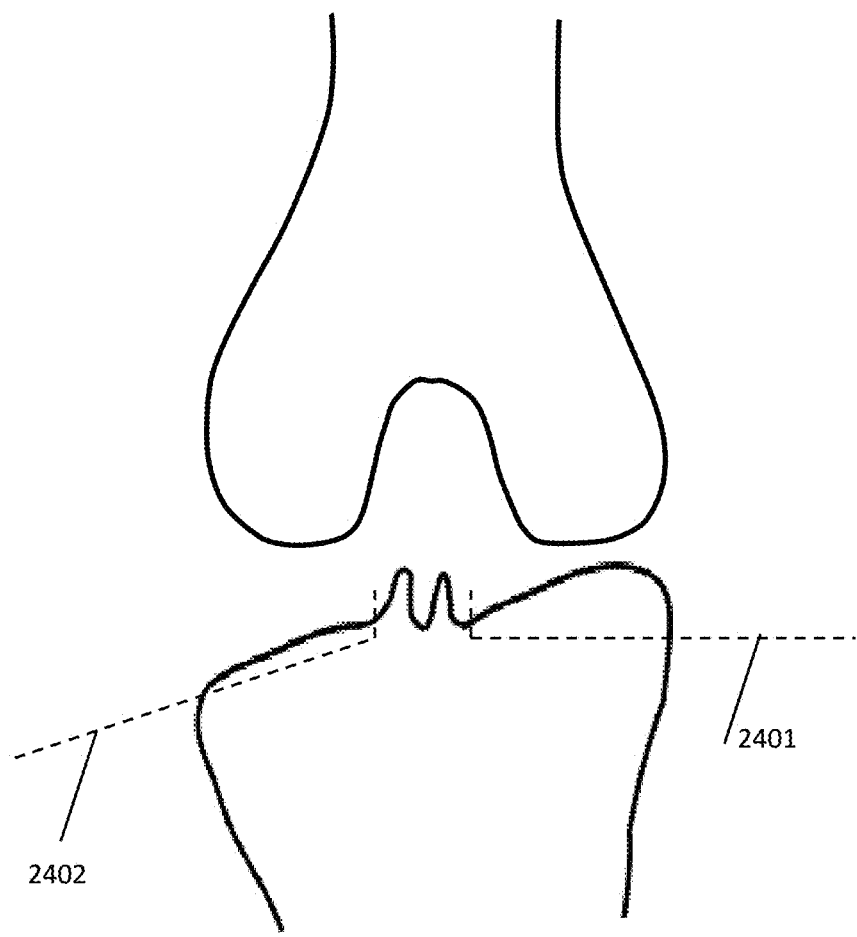
FIG. 24 depicts an exemplary knee joint with tibial cuts planned to differing levels and depths.
Figure 25:
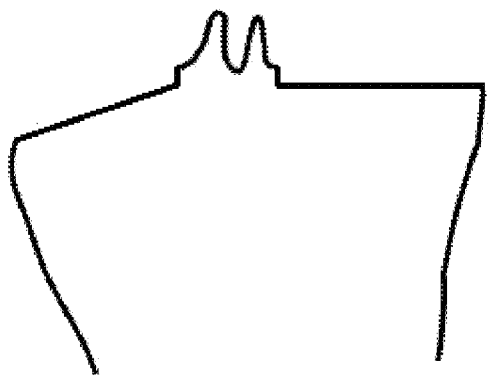
FIG. 25 depicts the knee joint of FIG. 24 in which a medial tibial section has been resected using a substantially horizontal cut and a lateral tibial section has been resected at a relatively steep angle.
Figure 26:
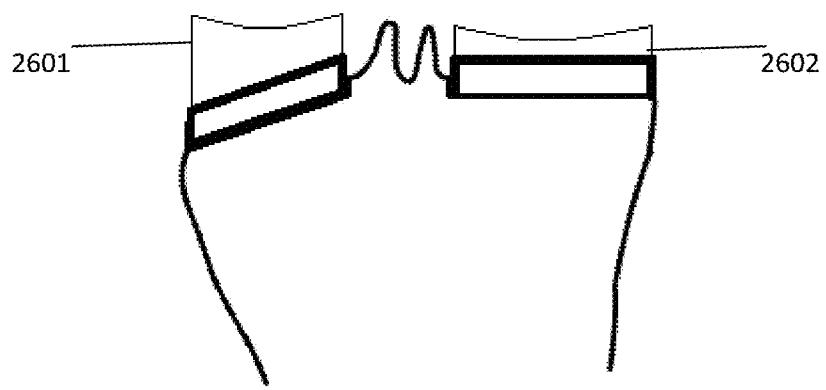
FIG. 26 depicts the tibia of FIG. 25, wherein a substantially thicker lateral insert than medial insert has been employed to create a desired resulting angulation.

In at least one alternative embodiment, various features of guide tools and surgical methods described herein can be used in conjunction with a wide variety of tibial trays, wedges and/or tibial inserts to accommodate the correction and/or reduction of extremely high varus and/or valgus angles in a given patient's anatomy. In such embodiments, a surgeon may choose to resect the medial and lateral portions of the tibia to differing levels and/or depths, as shown in FIG. 24, in which a medial tibial section has been resected using a substantially horizontal cut 2401, and a lateral tibial section has been resected at a relatively steep angle 2402, desirably removing a minimal amount of bone from the lateral side (see FIG. 25). After resection and creation of the respective tibial cut planes, the surgeon can choose to employ various combinations of tibial trays (e.g., separate medial and lateral trays) and/or inserts (e.g., dual inserts) to desirably create and/or replicate medial and lateral tibial condylar surfaces that improve and/or correct the varus and/or valgus angles of one or both of the patient's knee joints. In the embodiment shown in FIG. 26, a substantially thicker lateral insert 2601 (as compared to the thickness of the medial insert 2602) has been employed to create a desired resulting angulation for the knee implant. In one alternative embodiment, a single tibial tray may be used with a single or multiple tibial cuts, with a one or two piece insert having differing thickness on each of the medial/lateral portions in a similar manner.

In addition, valgus deformities may lead to patients with deformed or hypoplastic lateral condyles. In fact, hypoplastic lateral condyles may be present in 20% of patients that require knee replacement. An implant or tibial guide assemblies or other tools may be engineered from patient-specific data to address this deformity, by correcting or optimizing the lateral condyle, can include one or more expanded curvatures in one or more locations on the lateral condyle, relative to the patient's corresponding uncut medial or lateral condyle. For example, an implant may be engineered to include additional material on the outer, joint-facing surface of the implant component's lateral condyle. The expanded curvature(s) and/or material on the outside of the condyle can be used to design a material savings on the inside of the corresponding section of the implant component, for example, by maintaining a minimum material/implant thickness from the outside (joint-facing surface) to the inside (bone-facing surface) of the implant component. In this way, by adding material to the external contour of the implant component and maintaining a minimum material thickness of the implant component, bone preservation can be maximized. Specifically, with more material on the joint-facing surface of the implant and less material on the inner, bone-facing surface of the implant, the resection cuts are made closer to the surface of the bone. Accordingly, this approach uses the patient-adapted design of the implant component to both correct a condyle shape abnormality, such as a lateral condyle abnormality, such as hypoplasia, and to maximize bone preservation. In another embodiment, the deformity may be corrected by tailoring the tibial resection guide assemblies to have a unique medial and lateral assembly that will correct the angles. For example, the lateral condyle tibial resection guide may require smaller/lesser resection depth cut, different varus/valgus angle, or posterior/anterior angle than the medial tibial resection guide. Other tools and methods may be similarly designed to correct the deformity.

In an alternative embodiment, the tibial guide assembly, the joint implants, and other tools may be preoperatively designed and/or selected to correct the misalignment and/or obtain a proper mechanical alignment of a patient's limb. For example, based on the difference between the patient's misalignment and the proper mechanical axis, a knee implant and implant procedure can be designed and/or selected preoperatively to include implant and/or resection dimensions that substantially realign the patient's limb to correct or improve a patient's alignment deformity. In addition, the process can include selecting and/or designing one or more surgical tools (e.g., guide tools or cutting jigs) to direct the clinician in resectioning the patient's bone in accordance with the preoperatively designed and/or selected resection dimensions.

In certain embodiments, the degree of deformity correction that is necessary to establish a desired limb alignment is calculated based on information from the alignment of a virtual model of a patient's limb. The virtual model can be generated from patient-specific data, such 2D and/or 3D imaging data of the patient's limb. The deformity correction can correct varus or valgus alignment or antecurvatum or recurvatum alignment. In a preferred embodiment, the desired deformity correction returns the leg to normal alignment, for example, a zero degree biomechanical axis in the coronal plane and absence of genu antecurvatum and recurvatum in the sagittal plane.

The preoperatively designed and/or selected implant or implant component, resection dimension(s), and/or cutting guides, templates or cutting jig(s) can be employed to correct a patient's alignment deformity in a single plane, for example, in the coronal plane or in the sagittal plane, in multiple planes, for example, in the coronal and sagittal planes, and/or in three dimensions. For example, where a virtual model of a patient's misaligned lower limb is used to virtually correct the limb, a deformity correction can be achieved by designing and/or selecting one or more of a resection dimension, an implant component thickness, and an implant component surface curvature that adjusts the mechanical axis or axes into alignment in one or more planes. In various embodiments, a lower limb misalignment can be corrected in a knee replacement by designing or selecting one or more of a femoral resection dimension, a femoral implant component thickness, a femoral implant component surface curvature, a tibial resection dimension, a tibial implant component thickness, a tibial implant component insert thickness, and a tibial implant component surface curvature (or various combinations thereof) to adjust the femoral mechanical axis and tibial mechanical axis into alignment in the coronal plane.

Figure 27:
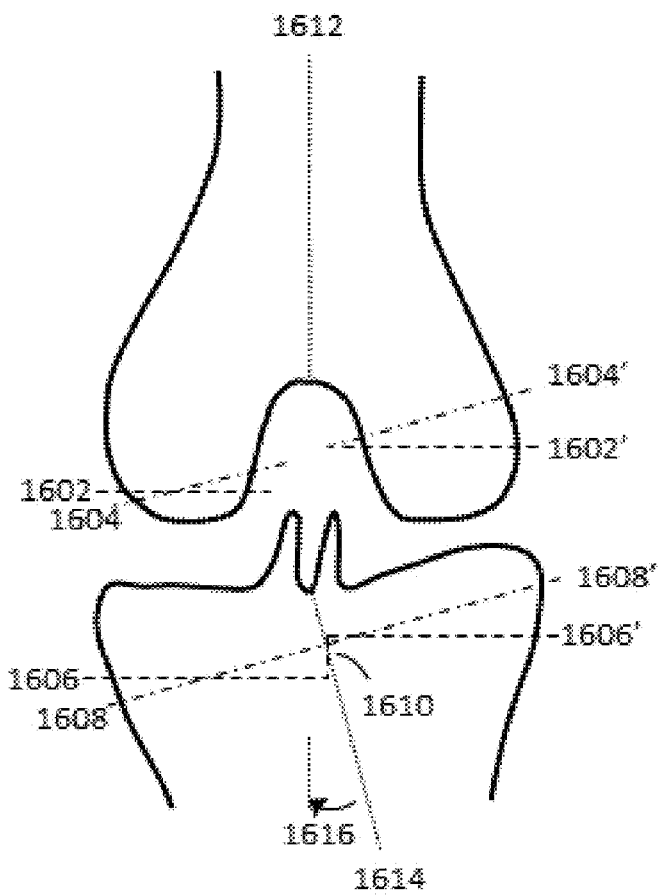
FIG. 27 illustrates a coronal plane of the knee with exemplary resection cuts that can be used to correct lower limb alignment in a knee replacement.

FIG. 27 illustrates a coronal plane of the knee with exemplary resection cuts that can be used to correct lower limb alignment in a knee replacement. As shown in the figure, the selected and/or designed resection cuts can include different cuts on different portions of a patient's biological structure. For example, resection cut facets on medial and lateral femoral condyles can be non-coplanar and parallel 1602, 1602', angled 1604, 1604', or non-coplanar and non-parallel, for example, cuts 1602 and 1604' or cuts 1602' and 1604. Similar, resection cut facets on medial and lateral portions of the tibia can be non-coplanar and parallel 1606, 1606', angled and parallel 1608, 1608', or non-coplanar and non-parallel, for example, cuts 1606 and 1608' or cuts 1606' and 1608. Non-coplanar facets of resection cuts can include a step-cut 1610 to connect the non-coplanar resection facet surfaces. Selected and/or designed resection dimensions can be achieved using one or more selected and/or designed guide tools (e.g., cutting jigs) that guide resectioning (e.g., guide cutting tools) of the patient's biological structure to yield the predetermined resection surface dimensions (e.g., resection surface(s), angles, and/or orientation(s)). In certain embodiments, the bone-facing surfaces of the implant components can be designed to include one or more features (e.g., bone cut surface areas, perimeters, angles, and/or orientations) that substantially match one or more of the resection cut or cut facets that were predetermined to enhance the patient's alignment. As shown in FIG. 27, certain combinations of resection cuts can aid in bringing the femoral mechanical axis 1612 and tibial mechanical axis 1614 into alignment 1616.

Figure 28:
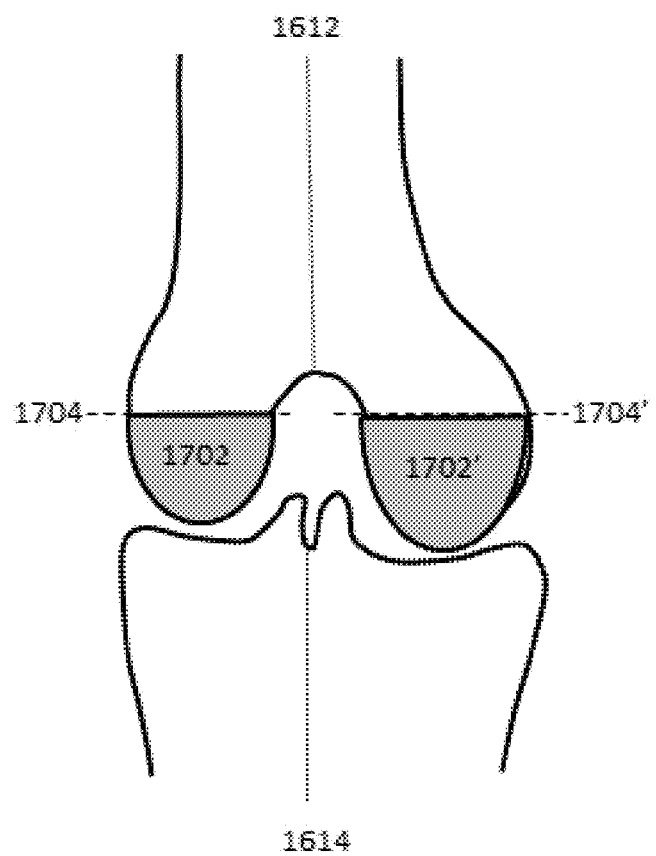
FIG. 28 depicts a coronal plane of a knee shown with femoral implant medial and lateral condyles having different thicknesses to help to correct limb alignment.

Alternatively, or in addition, certain implant features, such as different implant thicknesses and/or surface curvatures across two different sides of the plane in which the mechanical axes 1612, 1614 are misaligned also can aid correcting limb alignment. For example, FIG. 28 depicts a coronal plane of the knee shown with femoral implant medial and lateral condyles 1702, 1702' having different thicknesses to help to correct limb alignment. These features can be used in combination with any of the resection cut 1704, 1704' described above and/or in combination with different thicknesses on the corresponding portions of the tibial component. As described more fully below, independent tibial implant components and/or independent tibial inserts on medial and lateral sides of the tibial implant component can be used enhance alignment at a patient's knee joint. An implant component can include constant yet different thicknesses in two or more portions of the implant (e.g., a constant medial condyle thickness different from a constant lateral condyle thickness), a gradually increasing thickness across the implant or a portion of the implant, or a combination of constant and gradually increasing thicknesses.

Figure 29:
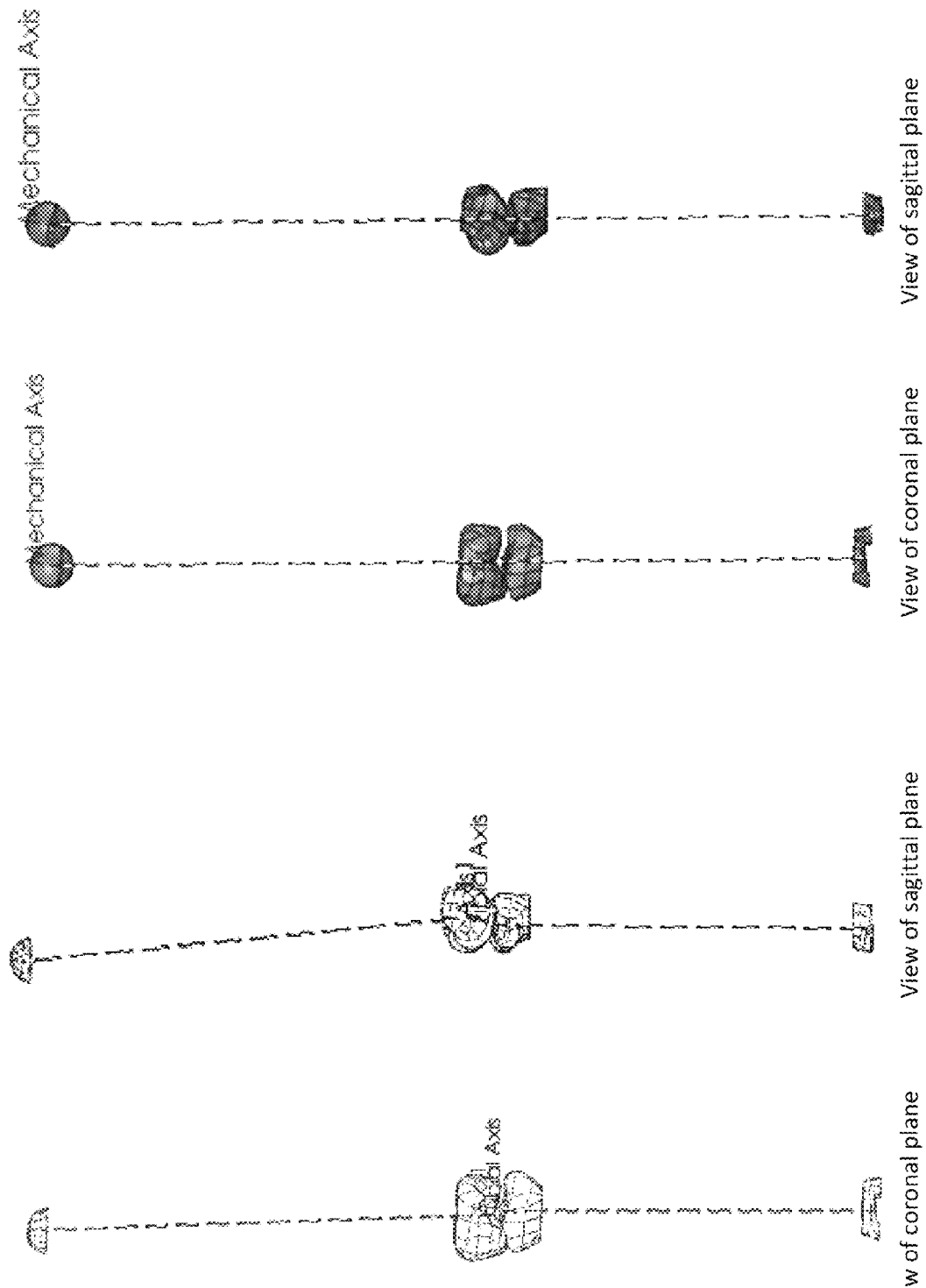
FIG. 29 illustrates a virtual model of a patient's limb that is misaligned in the sagittal plane, and a virtually corrected limb.

FIG. 29 illustrates a virtual model of a patient's limb that is misaligned in the sagittal plane, for example, a genu antecurvatum deformity, and the virtually corrected limb. The deformity correction can be achieved using a similar design approach as described above for a coronal plane deformity. However, the selection and/or design of one or more femoral resection dimensions, femoral implant component thicknesses, femoral implant component surface curvatures, tibial resection dimensions, tibial implant component thicknesses, tibial implant component insert thicknesses, and/or tibial implant component surface curvatures can be used to adjust the femoral mechanical axis and tibial mechanical axis into alignment in the sagittal plane (e.g., by altering corresponding features across the sagittal plane, for example, by altering anterior features relative to corresponding posterior features). Alignment deformities in both the coronal and sagittal planes, or in multiple planes about the mechanical axes, can be addressed by designing and/or selecting one or more resection dimensions, one or more implant component thicknesses, and/or one or more implant component surface curvatures.

In certain embodiments, an implant component that is preoperatively designed and/or selected to correct a patient's alignment also can be designed or selected to include additional patient-specific or patient-engineered features. For example, the bone-facing surface of an implant or implant component can be designed and/or selected to substantially negatively-match the resected bone surface. If resection dimensions are angled, for example, in the coronal plane and/or in the sagittal plane, various features of the implant component, for example, the component bone-facing surface, can be designed and/or selected based on an angled orientation into the joint rather than on a perpendicular orientation. For example, the perimeter of the tibial implant or implant component that substantially positively-matches the perimeter of the patient's cut tibial bone has a different shape depending on the angle of the cut. Similarly, with a femoral implant component, the depth or angle of the distal condyle resection on the medial and/or lateral condyle can be designed and/or selected to correct a patient alignment deformity. However, in so doing, one or more of the implant or implant component condyle width, length, curvature, and angle of impact against the tibia can be altered. Accordingly in certain embodiments, one or more implant or implant component features, such as implant perimeter, condyle length, condyle width, curvature, and angle is designed and/or selected relative to a sloping and/or non-coplanar resection cut.

Figure 14:
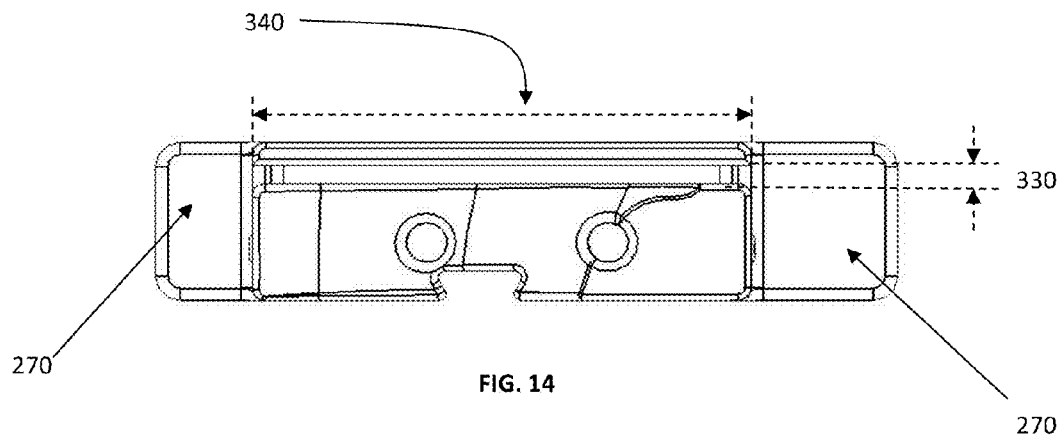
FIG. 14 depicts a back view of a "zero cut depth" guide box.

FIG. 14 depicts a back view of a tibial guide box. The back view shows a width 340 of the slot and a height 330 of the slot. The width of the guided slot 340 may also be specifically designed to control the width of the cut as required by the surgeon—it may be wider, it may be shorter or a specific cut shape. In various embodiments, the width of the preferred embodiment could substantially match the width of the specific implant components that will be placed on the tibia. The height 330 of the guided slot will desirably determine the cut depth of the tibial plateau, with the angulation of the slot similarly controlling and/or influencing the angulation of the cut plane (in both medial/lateral angulation as well as anterior/posterior angulation). In various embodiments, the cut plane height and/or angulation(s) may be patient specific as determined by each patient's anatomy, or some or all cut plane features could be "dialed in" using an adjustable mechanism as seen in FIG. 13B.

Figure 15:
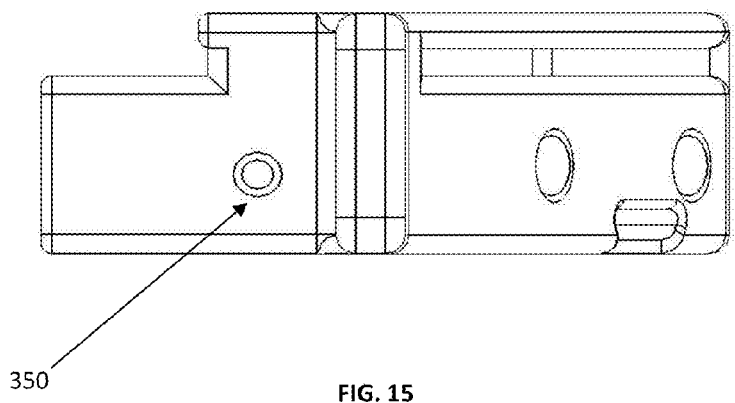
FIG. 15 depicts a side view of the guide box of FIG. 14.

FIG. 15 depicts a side view of a tibial guide box. The side view highlights the detent 350 which can used in various embodiments to lock into the detent receiver holes 230 (see FIG. 5). One or more of these detents can be placed on opposing sides of the box to ensure that an audible sound is heard (or other indication is provided) when locking the tibial guide box into the tibial guide housing.

Figure 16A:
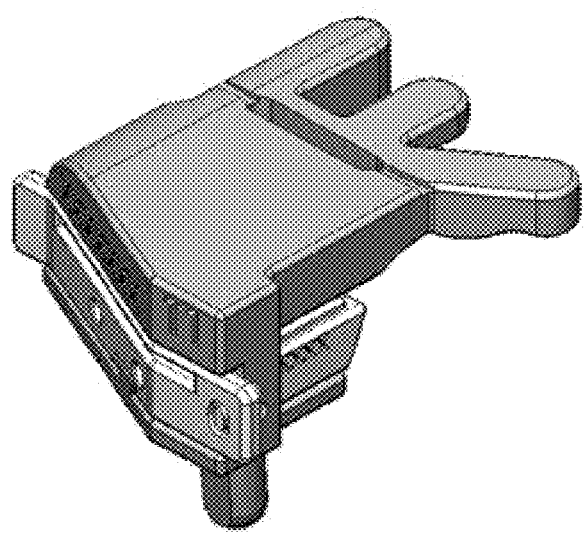
FIGS. 16A-16C depict isometric perspective, front plan, and back views of one embodiment of an assembled tibial guide assembly.
Figure 16B:
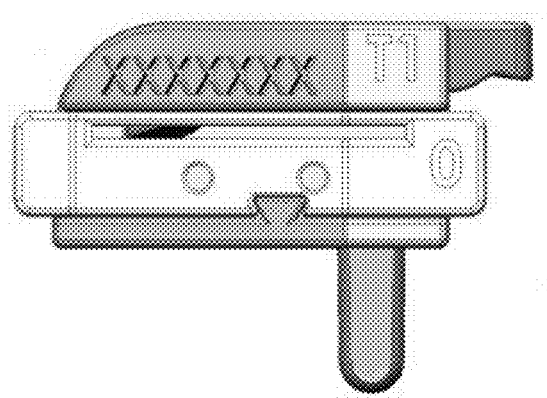
Figure 16C:
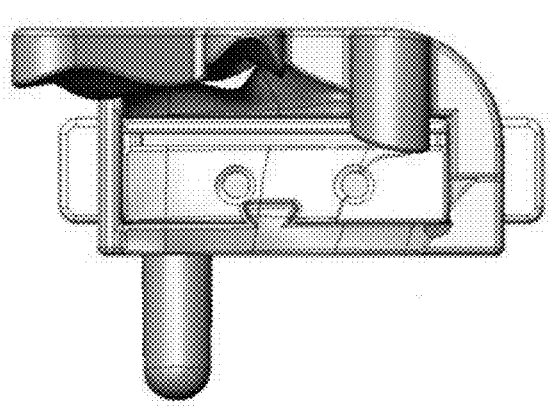

FIGS. 16A-16C depict an isometric view, a front view, and a back view of the tibial guide assembly, respectively. These shaded views show how an exemplary tibial guide box can fit within a corresponding tibial guide housing.

Improved Methods of Using a Tibial Guide Assembly

One preferred embodiment of the various teachings herein includes providing an apparatus and method for preparing the tibia for a tibial implant that significantly reduces the number of parts and component tools required to resect and prepare a tibial plateau, and desirably reduces the number of steps typically required in such a procedure. One of the many advantages of various embodiments described herein is that the assembly and associated components are modular, which allows the tibial housing to remain attached on the tibia, while multiple tibial guide boxes with varying cut depth dimensions, varus/valgus angles, and posterior/anterior cut angles can be utilized by the surgeon to make additional cuts and/or increase or modify the depth of cuts.

Figure 17A:
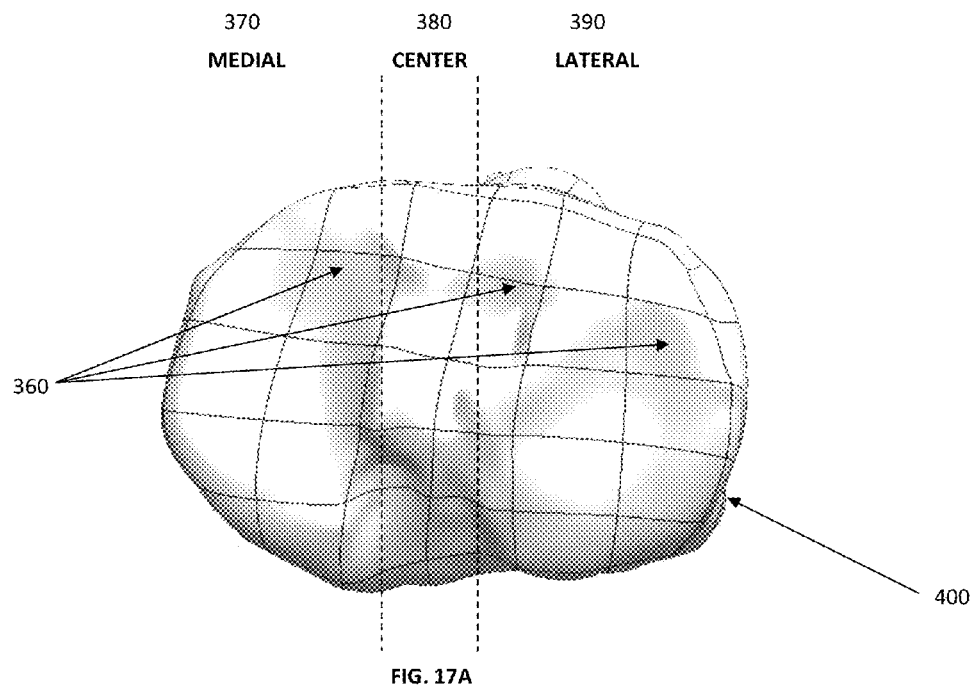
FIGS. 17A & 17B depict a top plan view and an anterior view of a patient's tibia remodeled by a computer system.

FIG. 17A depicts a top view of an uncut patient tibia 400 that has been modeled using a computer system. In this embodiment, there are three potential planes that the surgeon will be considering, which are the medial 370, the center 380 and the lateral 390 planes. Each of these planes has varying bone morphology that is shown by the articular ridges 360, and each plane may require a tibial guide assembly that attaches to the bone using the natural conforming bone anatomy adjacent thereto. The natural placement and positioning of an implant using the natural conforming bone anatomy will desirably provide the surgeon with a more secure tool to prepare and cut the tibial plateau.

Figure 17B:
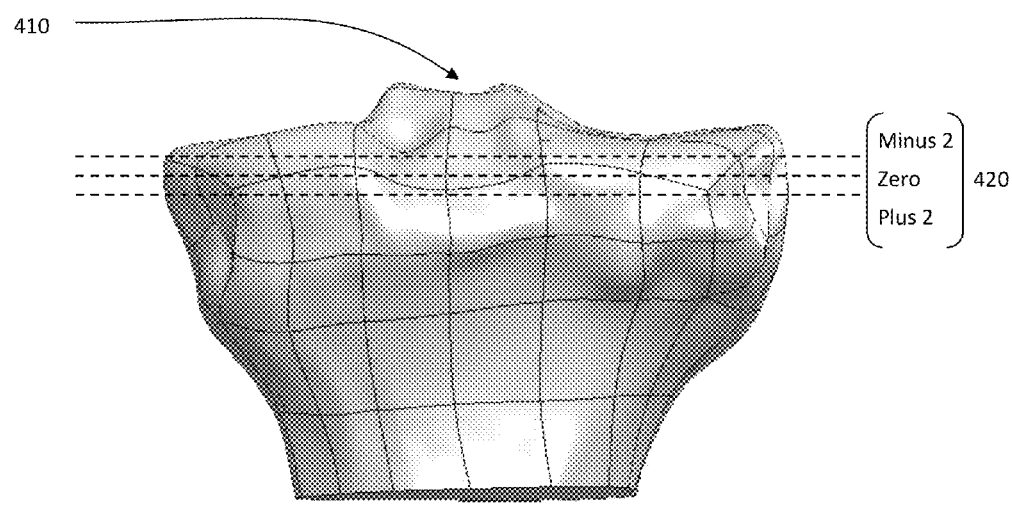

FIG. 17B shows an anterior view of a patient's uncut tibia and the medial and lateral intercondylar tubercle 410. This figure highlights the complex anatomy of a tibia and the varying exemplary cut planes 420 that a surgeon may desire in creating one or more desired cut planes to accept a tibial implant. The varying cut planes 420 show that the surgeon has already predetermined the cut depth, the varus/valgus angle, and the posterior/anterior angles that he or she wishes to make to prepare the tibia. However, once the surgeon has made one or more surgical access incisions and is able to directly visualize and/or observe the knee anatomy and the preparation required to cut the knee, the surgeon has the flexibility to adjust the predetermined cuts by using varying modular guide cut boxes with different cut depths and/or angles. For example, in one embodiment, if the surgeon wishes to cut less bone than originally predetermined, then the surgeon may choose the "Minus 2" tibial guide box instead of the "zero" guide box. This will allow the surgeon to cut less bone than what was originally predetermined.

Figure 18:
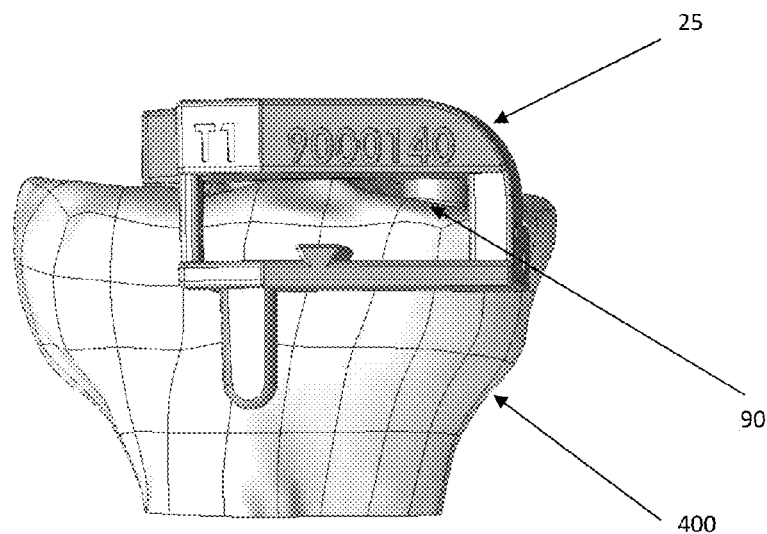
FIG. 18 depicts an anterior view of a tibial guide housing positioned on a medial side of a tibia.
Figure 19:
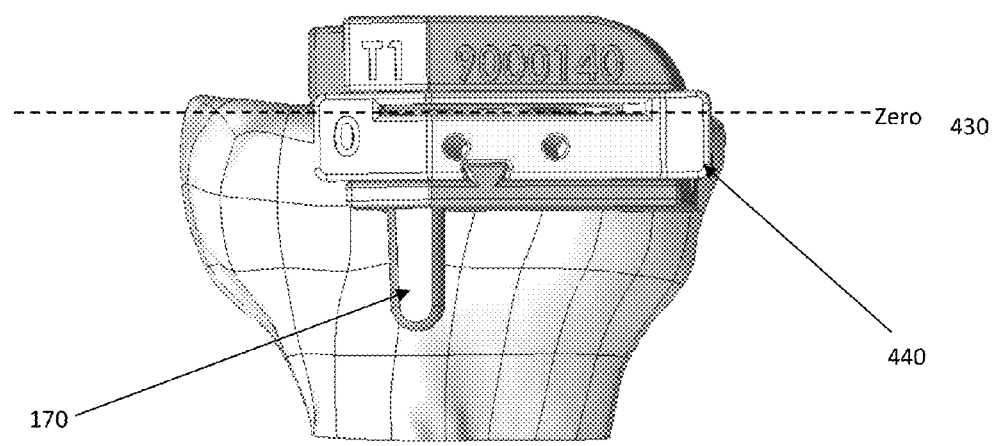
FIG. 19 depicts an anterior view of the tibial guide assembly and tibia of FIG. 18, with a "zero" tibial guide box inserted into the tibial guide housing.

FIG. 18 depicts an anterior view of a tibial guide housing 25 positioned on the medial side of the tibia 400 and showing the reference arms with a patient specific contact surface 90 conforming to the natural anatomy of the bone; the resection guide is aligned primarily to match natural landmarks of the articular surface or other features of the tibial plateau. Once a desired natural conforming position is found, the surgeon may score the articular surface to reach the subchondral bone to ensure proper positioning and placement, if desired. After the position has been determined, the surgeon may choose to determine the patient's mechanical axis with reference to their anatomical axis with an alignment rod or equivalent systems. For example, an alignment rod may be attached to a tibia guide housing 170 as shown in FIG. 19 and can extend to the patient's ankle to be parallel to the tibia's mechanical axis. The alignment rod system may be designed to be telescoped between its two connection points, which assists with the alignment of the patient's mechanical axis and provides preferred positioning that may be adjustable. The use of the alignment rod may, in various embodiments, provide the surgeon with an additional confirmation that the housing 170 is aligned with the correct patient-specific anatomy.

Figure 20:
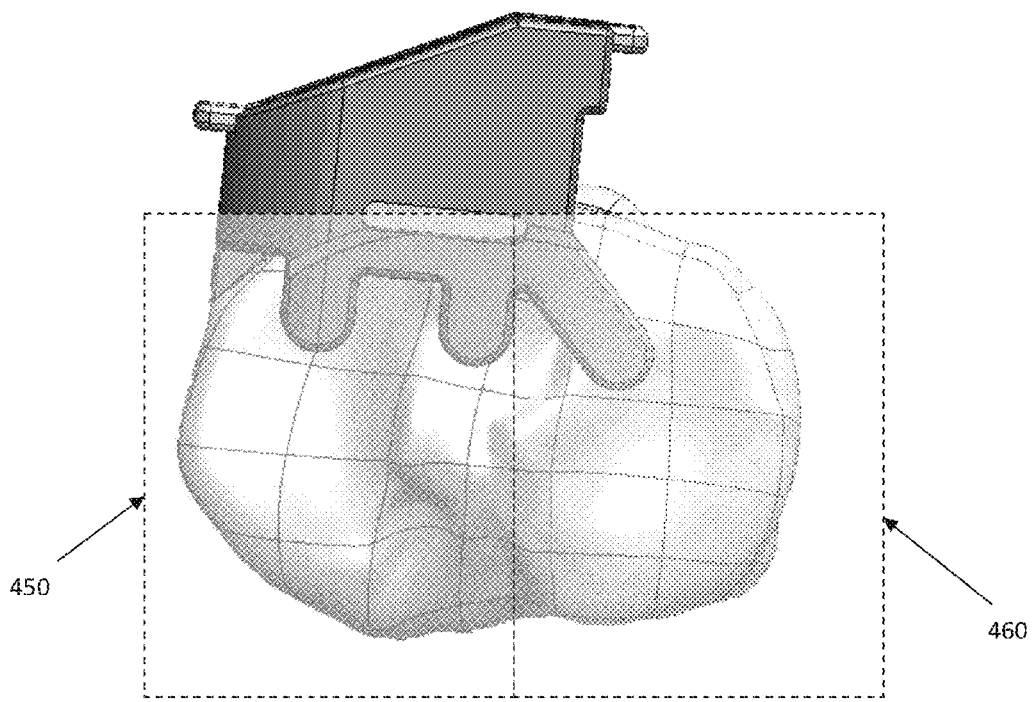
FIG. 20 depicts a top plan view of a tibial guide assembly, with exemplary medial and lateral cut planes.
Figure 21:
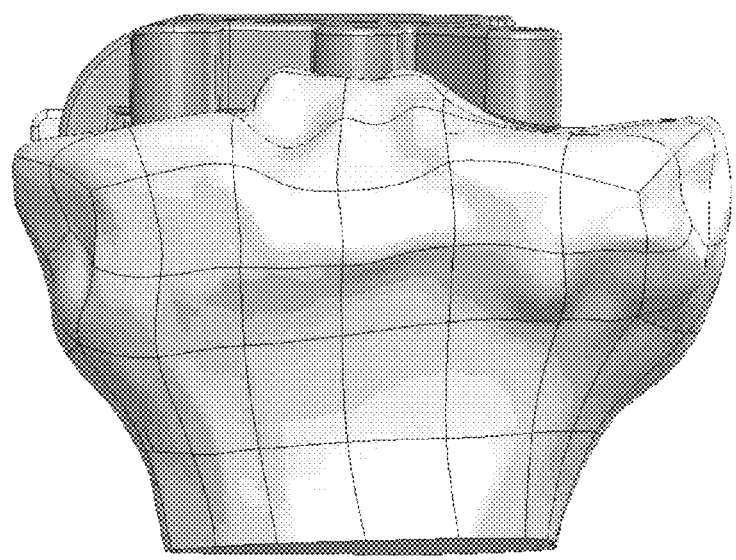
FIG. 21 depicts a posterior view of a tibial guide assembly positioned on a medial side of a tibia.

Once the alignment system is positioned, the tibial guide housing may be attached to the tibia using known methods and tools available in the OR, or provided in an instrument kit; and such attachment may include securement using a pin arrangement, e.g., by fitting one or more pins through appropriate openings in the tibial guide box (see FIG. 6) and/or the tibial guide housing. In various embodiments, after attaching the tibial guide housing to the anterior surface of the bone, a predetermined or adjusted tibial guide box may be inserted into the tibial guide housing. A reciprocating saw or similar cutting device can be fitted through a cutting guide slot in the tibial guide box and reciprocated or otherwise manipulated or employed to cut across the medial side 450 (see FIG. 20) tibial plateau with a predetermined or adjusted cutting plane 430. If the surgeon is satisfied with the cut, the entire tibial guide assembly may be removed and, if desired, the guide pins may be left in place and the steps may be repeated for the lateral side of the tibia using another lateral side tibial guide assembly. FIG. 20 depicts the top view of the tibial guide assembly and exemplary medial 450 and lateral 460 cut planes.

Figure 22:
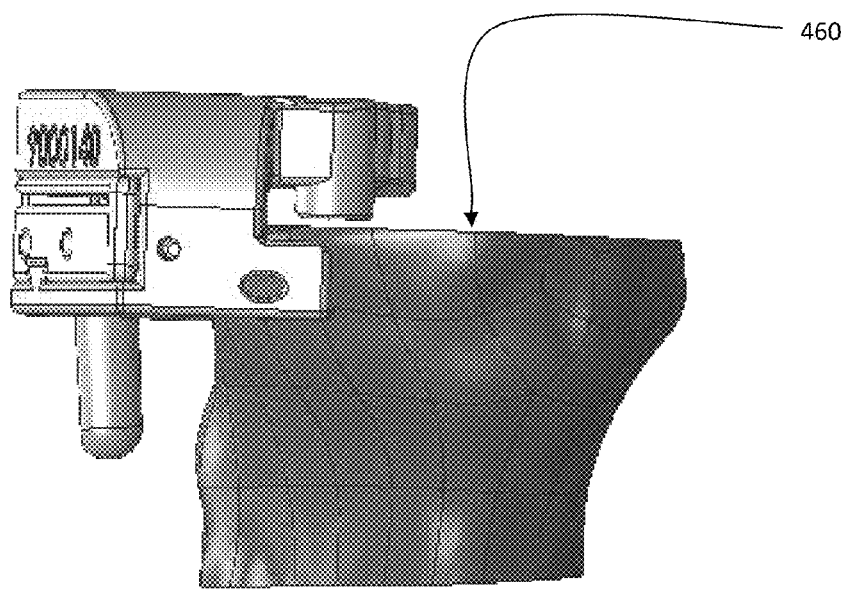
FIG. 22 depicts a side view of a tibial guide assembly, with both medial and lateral sides of a tibia resected.

FIG. 22 depicts a side view of a tibial guide assembly after both medial 450 and lateral 460 sides of the tibia have been resected; this figure highlights the uniformity of the entire cut tibial surface 460 when using the tibial guide assembly and captured/guided cut boxes. In various alternative embodiments, the medial and lateral cut planes may not be parallel, offset, and/or coplanar. At this time, the surgeon can remove the tibial guide assembly leaving the positioning pins for both the medial and lateral cuts in place to conduct a trialing and fixation of the knee prosthesis. The trialing may involve fitting the prosthesis components to the prepared surfaces and checking the patient's range of motion, alignment, and the ligament stability that will approximate the range of motion of a natural knee. In at least one exemplary embodiment, the proximal tibial end can preferably be first fitted with a variety of templates and measuring tools and be followed by fitting the femur portion of the prosthesis to the prepared distal femur end.

Figure 23:
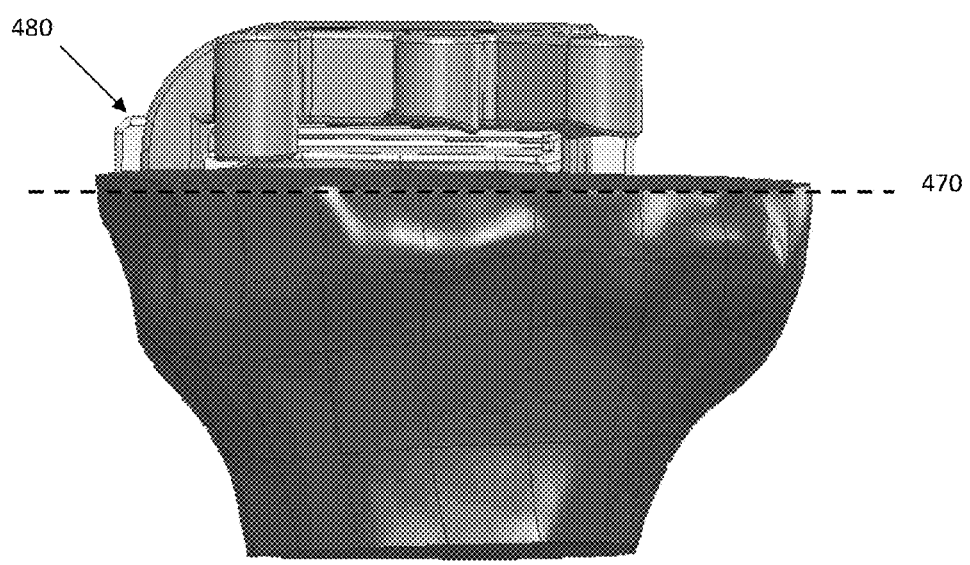
FIG. 23 depicts a posterior view of the tibial guide assembly with an optional cut plane.

If various trialing steps do not optimally fit the trial implant prosthesis, additional cuts on the tibia may be made. For example, if the knee is tight in extension and flexion, the tibia may be further resected as necessary using the tibial guide assembly and adjusting the tibial guide boxes 480 (in FIG. 23) to preferred cut depth and angles. If the knee is tight in extension and balanced in flexion, the distal femur may be cut. Lastly, if the knee is tight in flexion and balanced in extension, it is possible that the surgeon may choose a tibial guide cut box to add posterior/anterior slope to the already cut tibial surface. However, many other combinations may be found to optimally adjust the cut depth 470 of the tibia resected surface using the guide boxes and combinations of guide boxes with varying dimensions or angles.

Once the proper alignment and balancing of the trial implants have been performed, the surgeon may secure the actual knee joint components and patella prosthesis to the patella. The result can be tested and thereafter the incision into the knee can be appropriately closed and dressed.

What is claimed is:

1. A system for preparing a tibial plateau of a tibia of a patient, the system comprising: a tibial guide housing, the tibial guide housing comprising: a top side generally opposite a bottom side and a front side generally opposite a back side; a first reference arm having a patient-specific contact surface configured to conform to a first portion of a superior surface of the tibia; a second reference arm having a patient-specific contact surface configured to conform to a second portion of the superior surface of the tibia; and at least one pin hole configured to accommodate insertion of a pin through the tibial guide housing and into the tibia, wherein the back side includes a patient-specific contact surface configured to conform to a portion of the anterior surface of the tibia; one or more tibial cutting guide boxes, each of the one or more tibial cutting guide boxes comprising: a patient-specific contact surface configured to conform to a portion of an anterior surface of the tibia; a guide aperture configured to accommodate a surgical cutting tool and guide the cutting tool along a cutting plane having a predetermined cut depth and angle; and at least one pin hole configured to accommodate a pin passing into the tibia.

2. The system of claim 1, wherein the one or more tibial cutting guide boxes are each configured for releasable securement within the tibial guide housing.

3. The system of claim 1, including at least two tibial cutting guide boxes, wherein each of the at least two tibial cutting guide boxes has a different predetermined cut depth.

4. The system of claim 1, wherein the tibial guide housing further comprises a third reference arm having a patient-specific contact surface configured to conform to a third portion of the superior surface of the tibia.

5. A method of preparing a tibial plateau of a tibia of a knee joint of a patient for implantation of at least one prosthesis, the method comprising: providing a tibial guide housing, the tibial guide housing including: a first reference arm having a patient-specific contact surface configured to conform to a first portion of a superior surface of the tibia; a second reference arm having a patient-specific contact surface configured to conform to a second portion of the superior surface of the tibia; and a back side having a patient-specific contact surface configured to conform to a portion of an anterior surface of the tibia; providing a first tibial cutting guide box, the first tibial cutting guide box including: a patient-specific contact surface configured to conform to a portion of the anterior surface of the tibia; and a guide aperture configured to accommodate a surgical cutting tool and guide the cutting tool along a cutting plane having a predetermined cut depth and angle; positioning the tibial guide housing on the tibia such that each of the patient-specific contact surfaces of the tibial guide housing achieves a conforming fit with the tibia; positioning the first tibial cutting guide box such that the patient-specific contact surface of the first tibial cutting guide box achieves a conforming fit with the tibia; and inserting a cutting device through the guide aperture and cutting a portion of the tibia along the cutting plane.

6. The method of claim 5, further comprising inserting the first tibial cutting guide box into an opening of the tibial guide housing.

7. The method of claim 5, further comprising removing the first tibial cutting guide box from the tibial guide housing.

8. The method of claim 5, further comprising selecting the first tibial cutting guide box from a plurality of tibial cutting guide boxes, each including a guide aperture having a different predetermined cut depth.

9. The method of claim 5, further comprising: positioning a prosthesis component on a cut surface of the tibia; and checking a state of the knee joint, wherein the state of the knee joint is selected from the group consisting of ligament stability of the knee joint, range of motion of the knee joint, alignment of the knee joint, and combinations thereof.

10. The method of claim 9, further comprising: selecting a second tibial cutting guide box from a plurality of tibial cutting guide boxes, each including a guide aperture having a different predetermined cut depth, based, at least in part, on the checking a state of the knee joint; and positioning the second tibial cutting guide box such that a patient-specific contact surface of the second tibial cutting guide box achieves a conforming fit with a portion of the anterior surface the tibia.

11. The method of claim 5, including cutting a medial portion of the tibia or a lateral portion of the tibia.

* * * * *